United States Patent [19]

Elkins et al.

[11] Patent Number: 4,691,762
[45] Date of Patent: Sep. 8, 1987

[54] PERSONAL TEMPERATURE CONTROL SYSTEM

[75] Inventors: William Elkins, San Jose; Eugene W. Connell, Los Gatos; Robert E. Short, Cupertino, all of Calif.

[73] Assignee: Life Support Systems, Inc., Mountain View, Calif.

[21] Appl. No.: 839,737

[22] Filed: Mar. 14, 1986

Related U.S. Application Data

[63] Continuation of Ser. No. 514,771, Apr. 1, 1983, abandoned.

[51] Int. Cl.$^4$ ............................................. A61F 7/00
[52] U.S. Cl. ................................. 165/46; 128/380; 128/400
[58] Field of Search ................. 165/46, 103; 128/380, 128/381, 400

[56] References Cited

U.S. PATENT DOCUMENTS

| | | | |
|---|---|---|---|
| 3,744,555 | 7/1973 | Fletcher et al. | 165/46 |
| 3,869,871 | 3/1975 | Rybalko et al. | 165/46 X |
| 3,995,621 | 12/1976 | Fletcher et al. | 128/2 H |
| 4,149,529 | 4/1979 | Copeland et al. | 128/24.1 |
| 4,196,772 | 4/1980 | Adamski et al. | 165/46 |
| 4,204,613 | 5/1980 | Terzian et al. | 165/163 X |

*Primary Examiner*—William R. Cline
*Assistant Examiner*—Richard R. Cole
*Attorney, Agent, or Firm*—Thomas M. Freiburger

[57] ABSTRACT

A personal temperature control system including a first heat exchanger adapted to be worn as a garment and a second heat exchanger adapted to interact with a temperature source, the first and second heat exchangers being interconnected through a pump and reservoir unit. The first heat exchanger together with the pump and reservoir are portable and in one embodiment the second heat exchanger is constructed to be fully portable. Specific devices including automatic quick release couplings interconnect the first heat exchanger to the second heat exchanger through the pump and reservoir. The fabrication of the first heat exchanger in helmet and vest portions is disclosed together with a control display unit housing the pump and reservoir and including an adjustable flow valve connected in parallel with the second heat exchanger. A preferred embodiment of the adjustable flow valve provides non-linear change in rate of flow upon adjustment.

12 Claims, 44 Drawing Figures

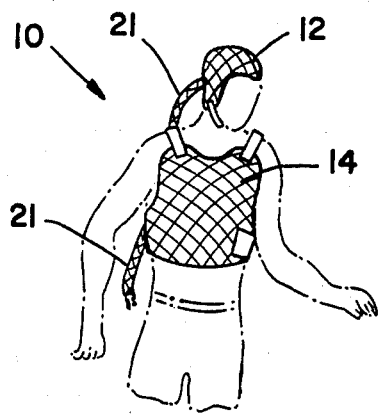
FIG_1A
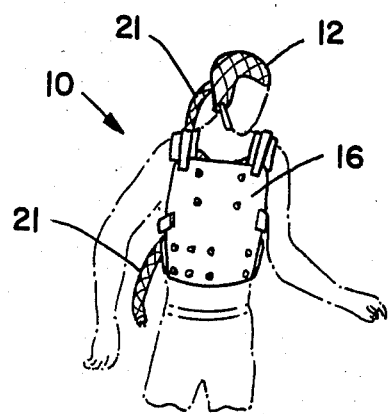
FIG_1B
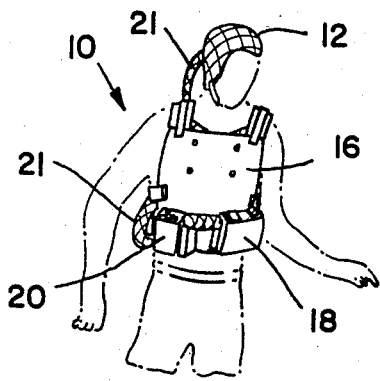
FIG_1C
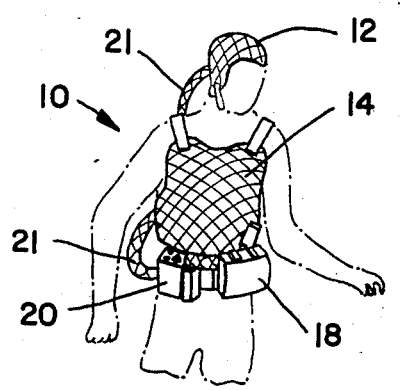
FIG_1D
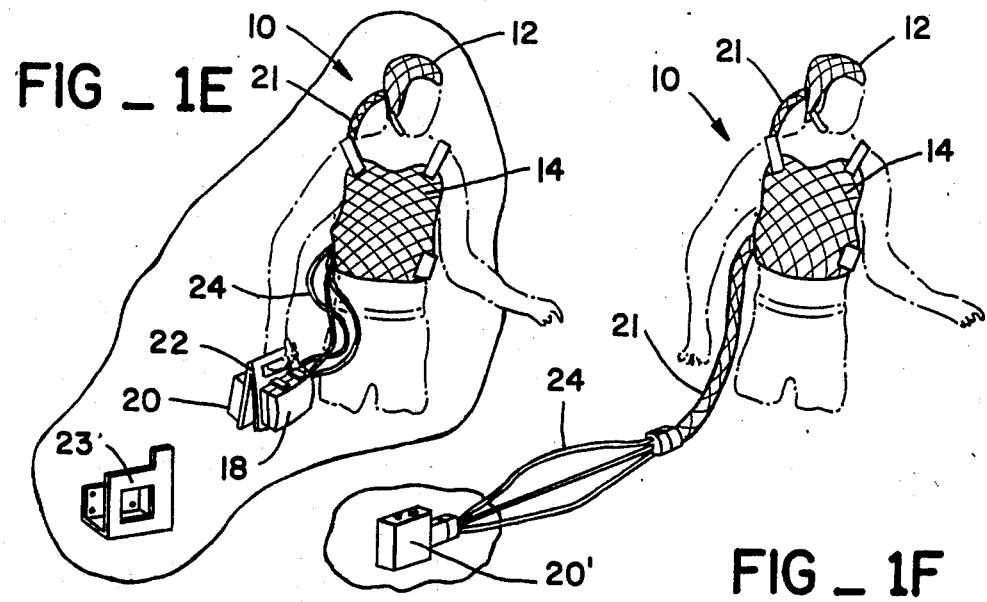
FIG_1E    FIG_1F

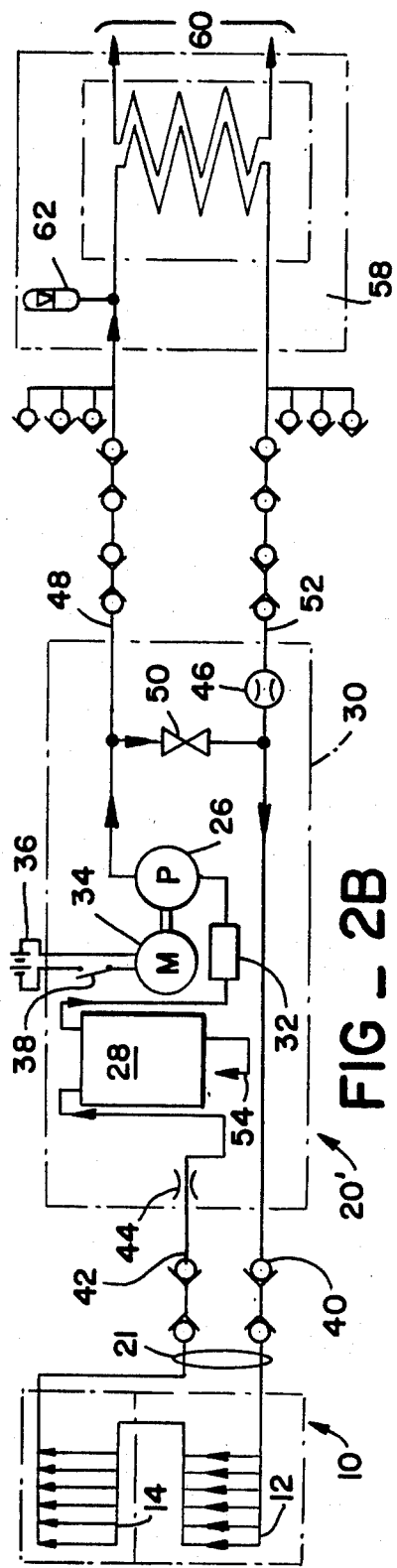
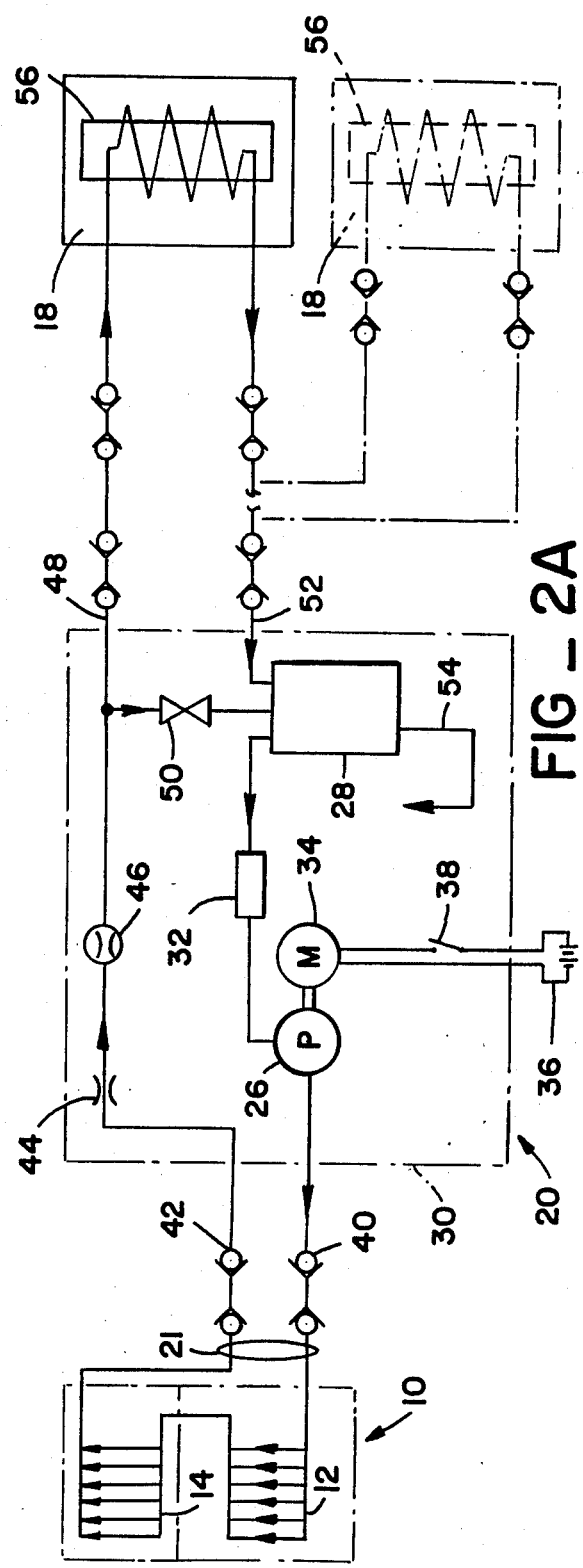

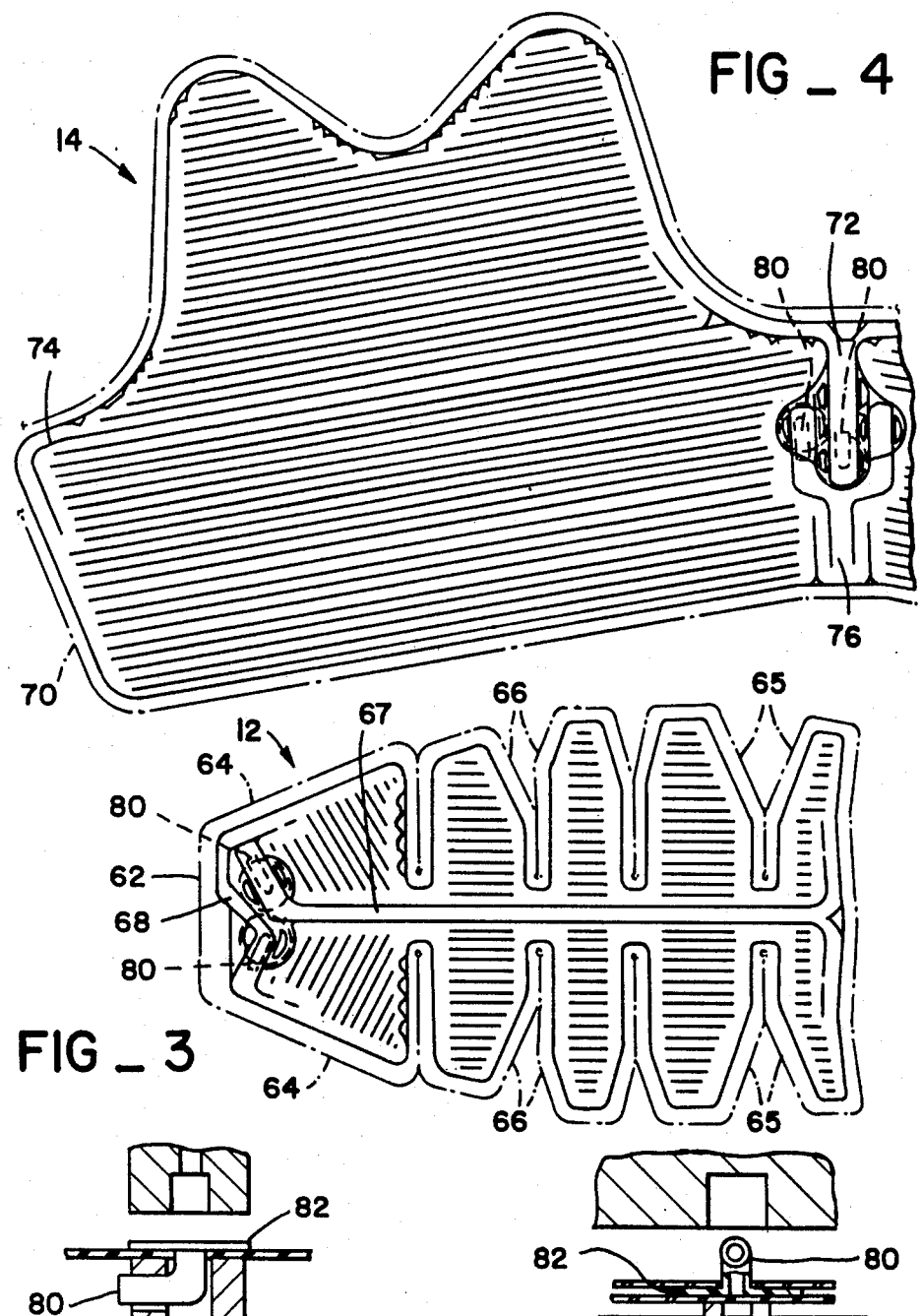

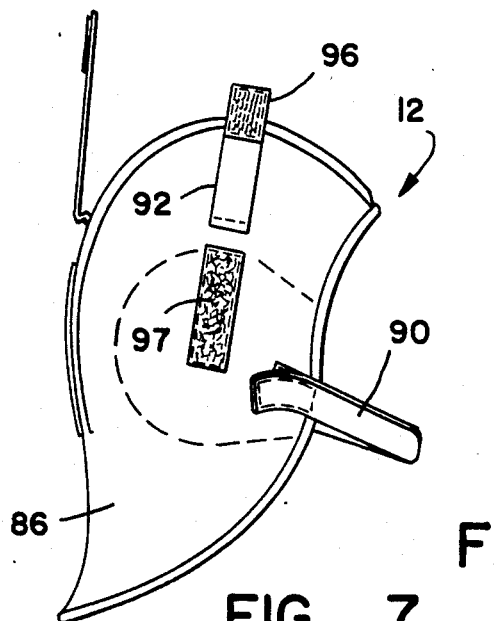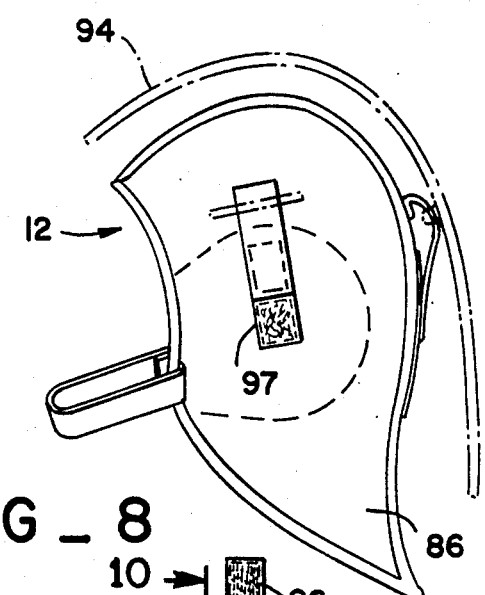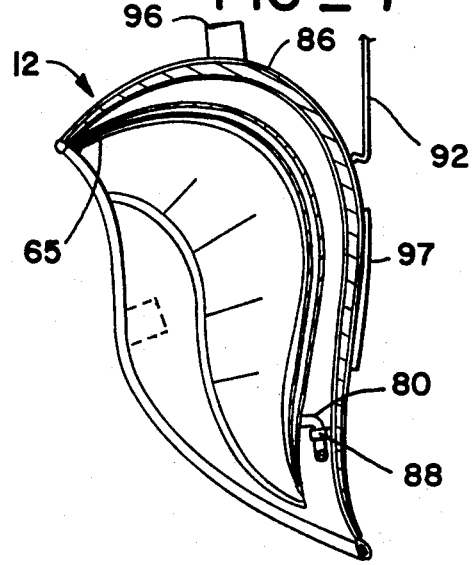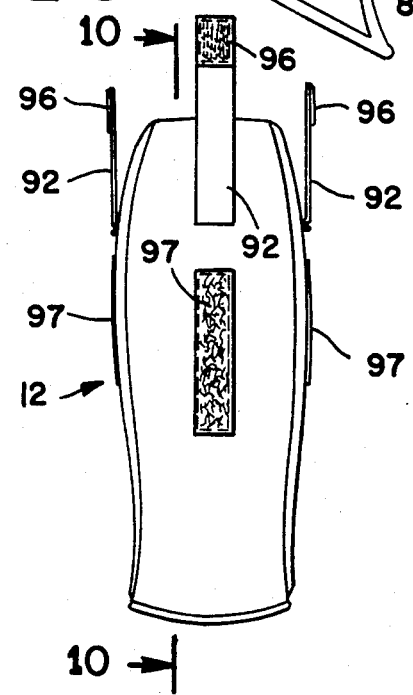

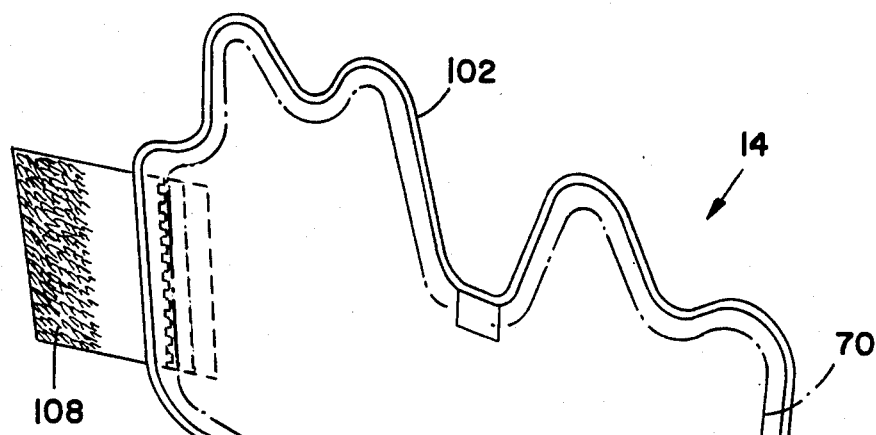
FIG_11
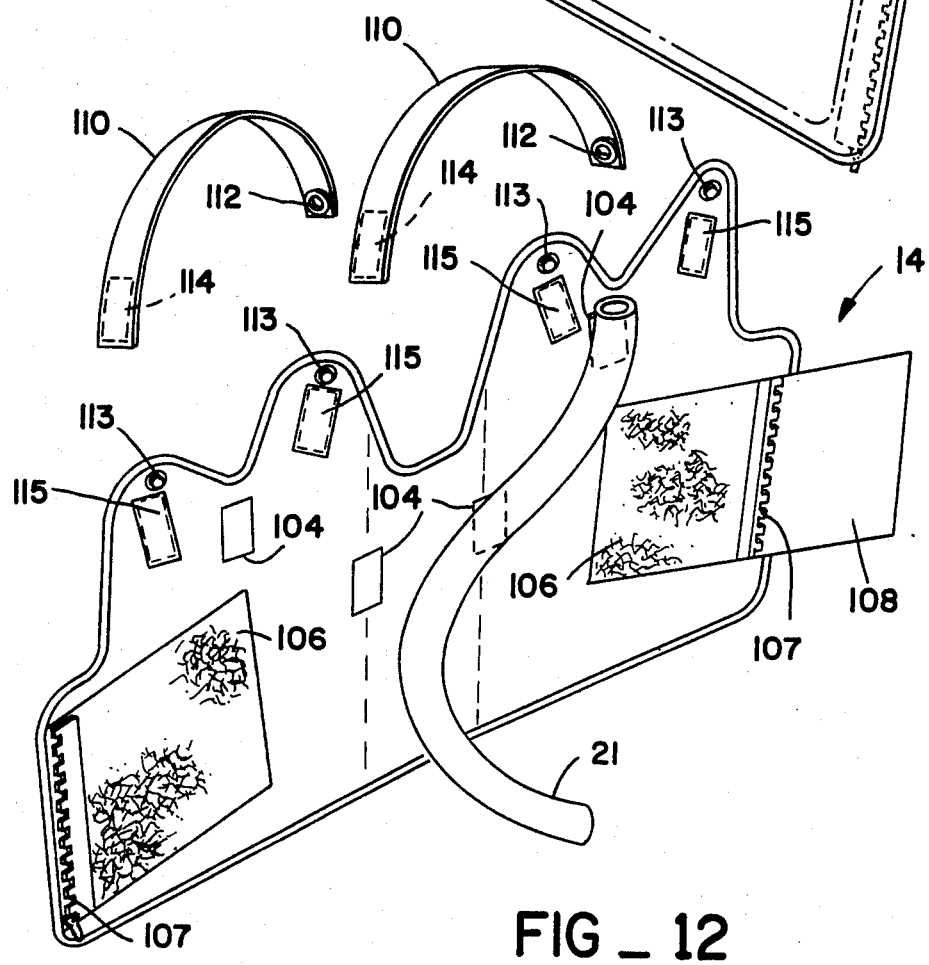
FIG_12

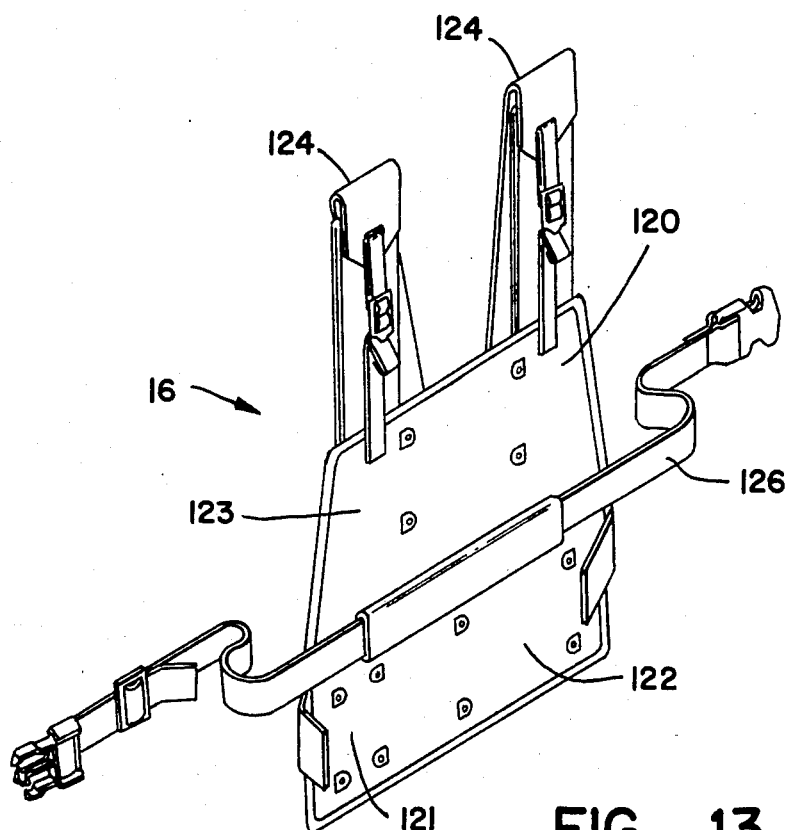
FIG_13
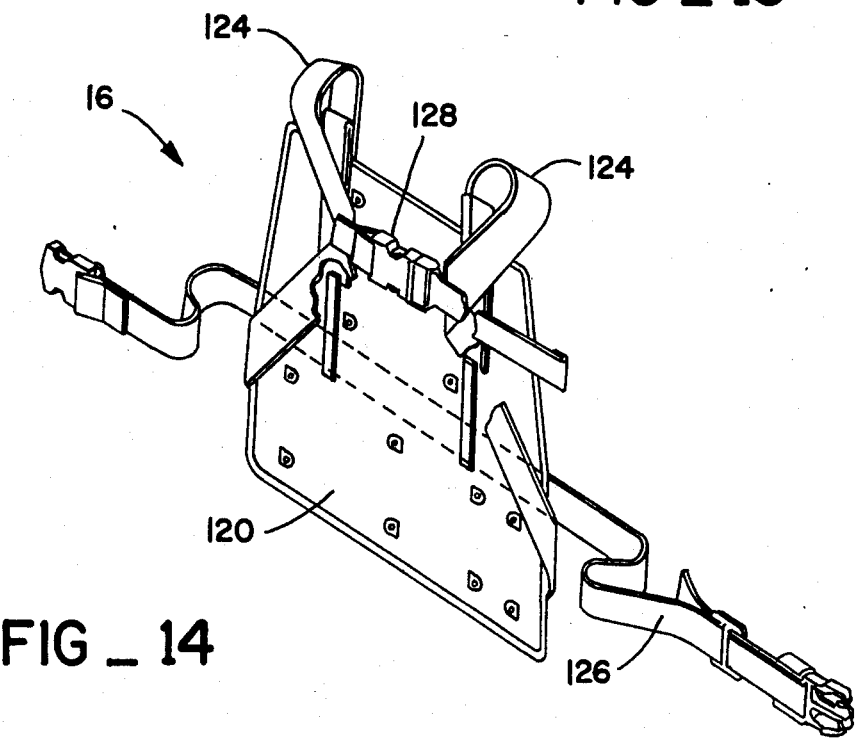
FIG_14

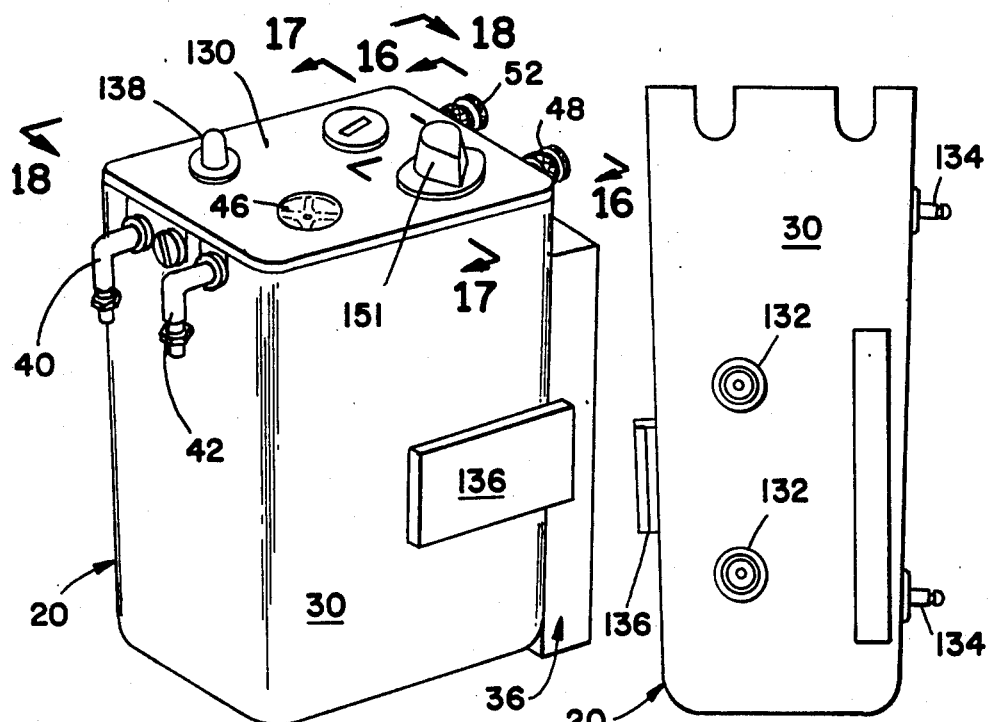
FIG_15    FIG_16
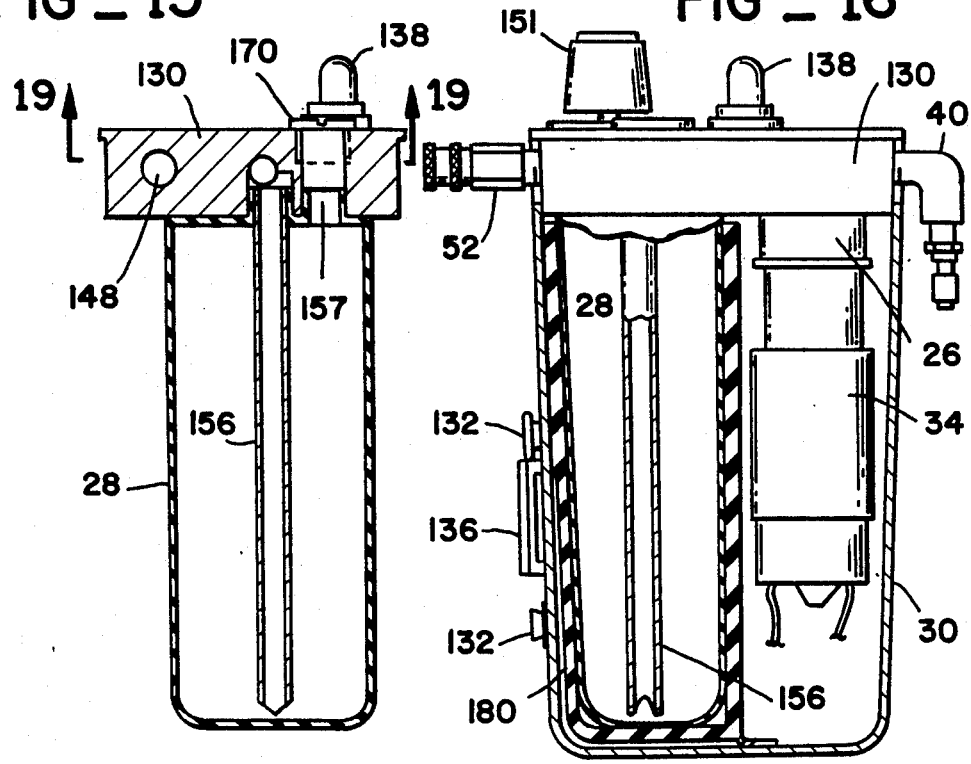
FIG_17    FIG_18

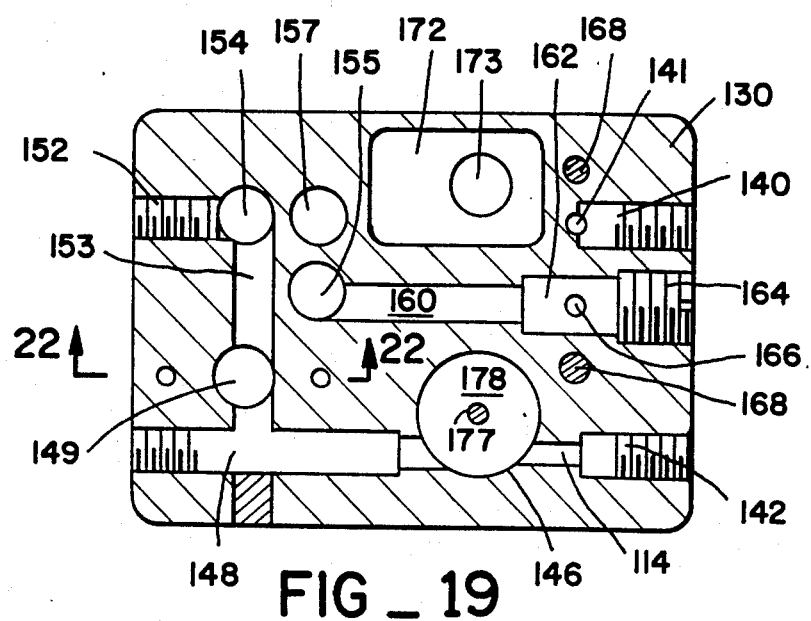
FIG_19
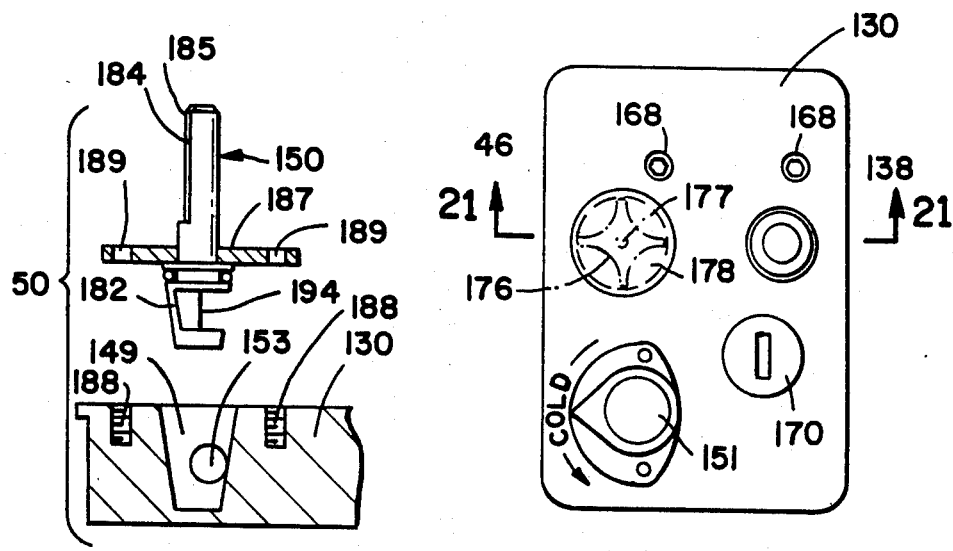
FIG_22
FIG_20
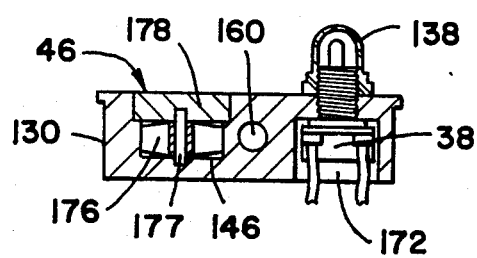
FIG_21

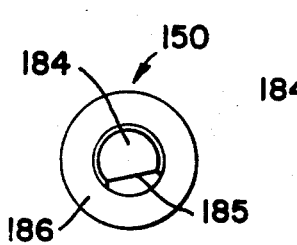
FIG_24
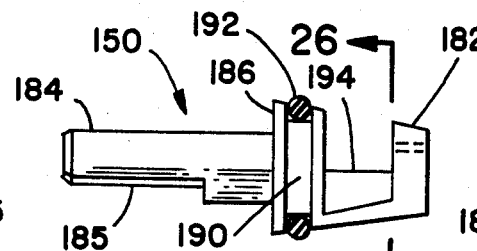
FIG_23
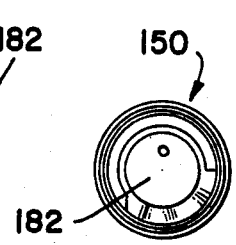
FIG_25
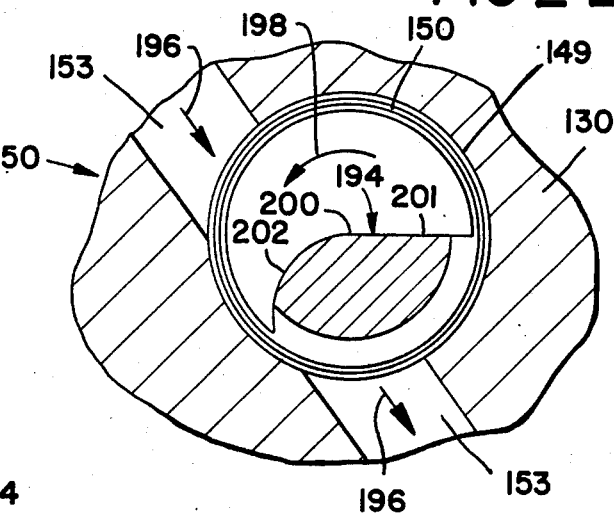
FIG_26
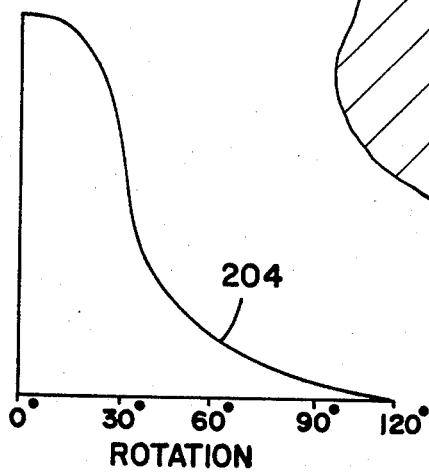
FIG_27
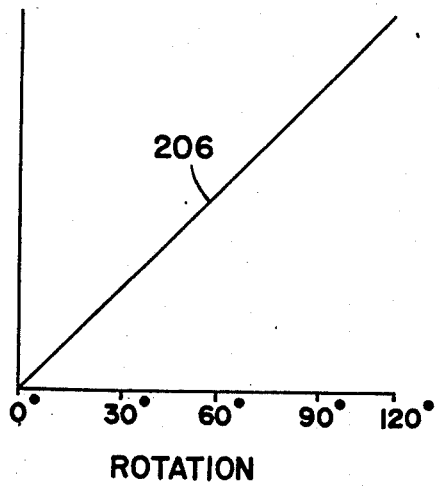
FIG_28

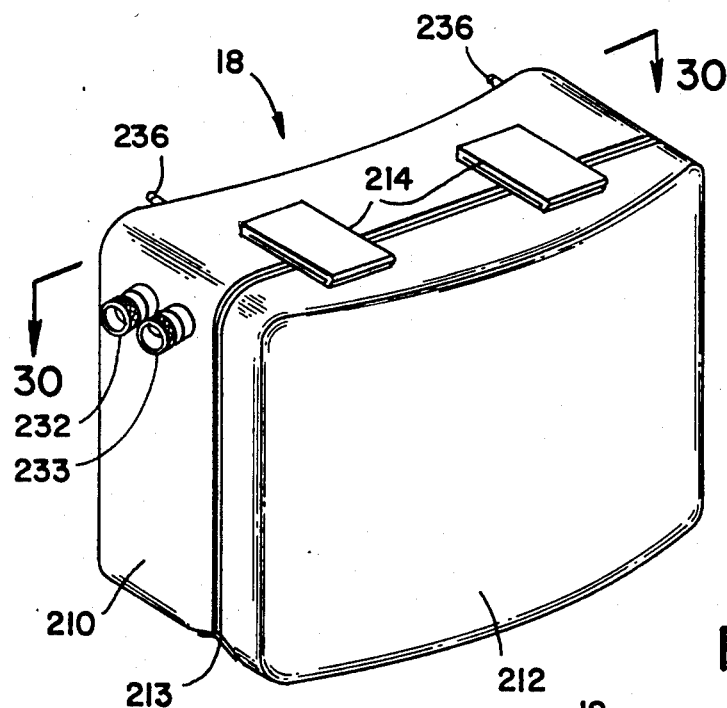
FIG _ 29
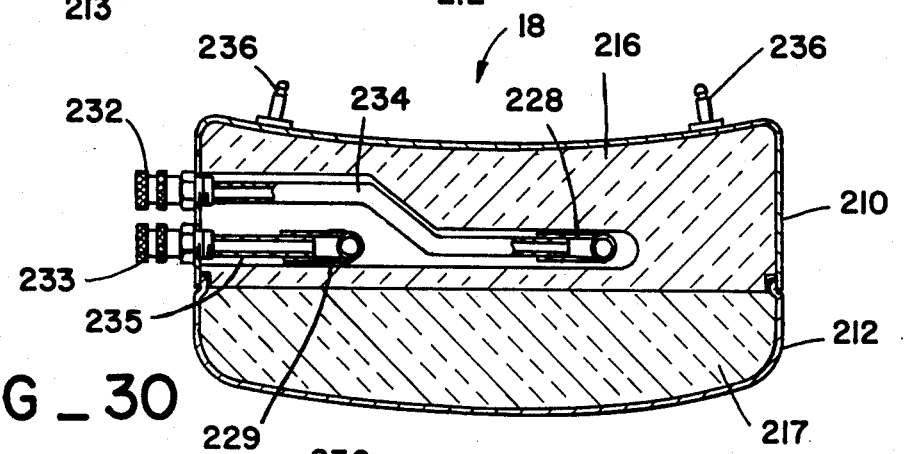
FIG _ 30
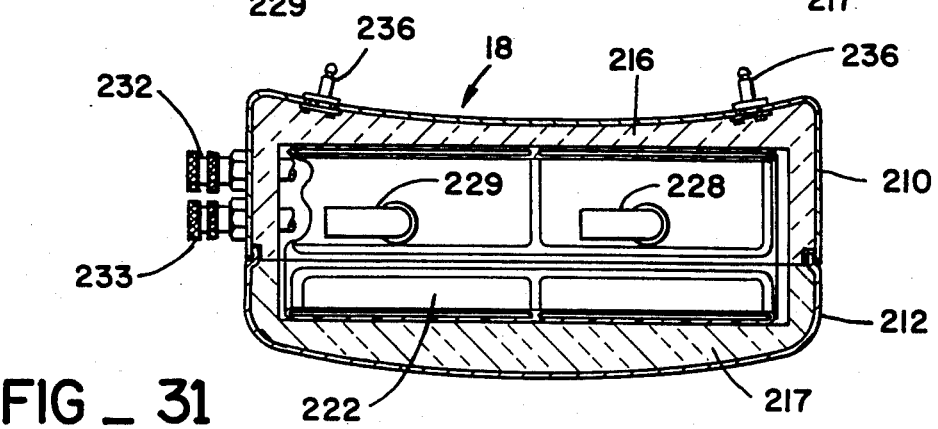
FIG _ 31

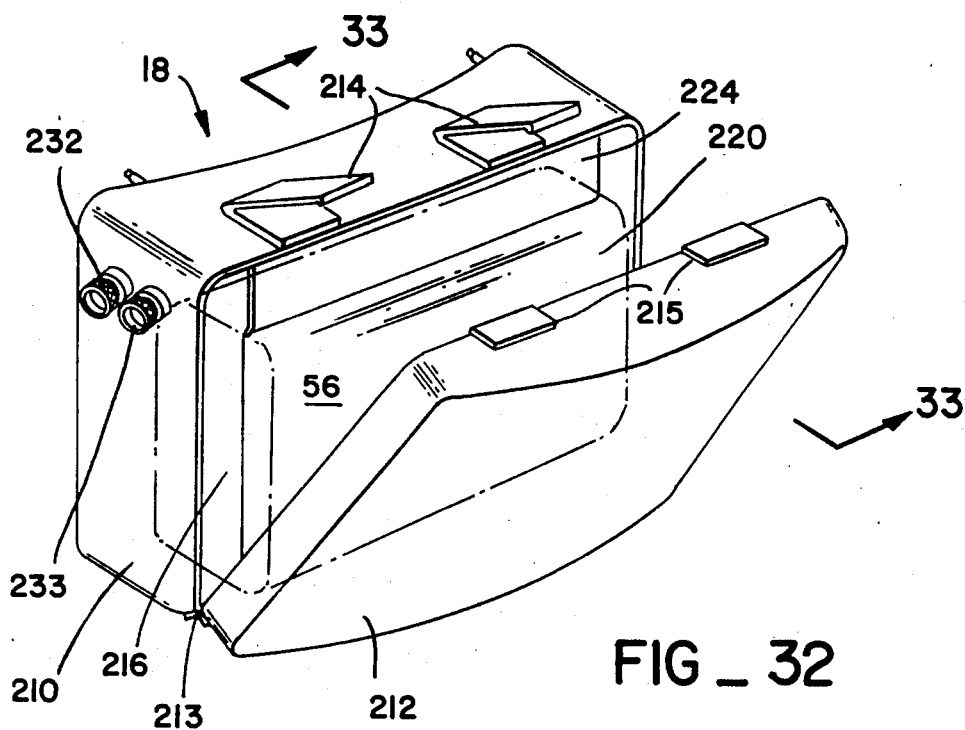
FIG_32
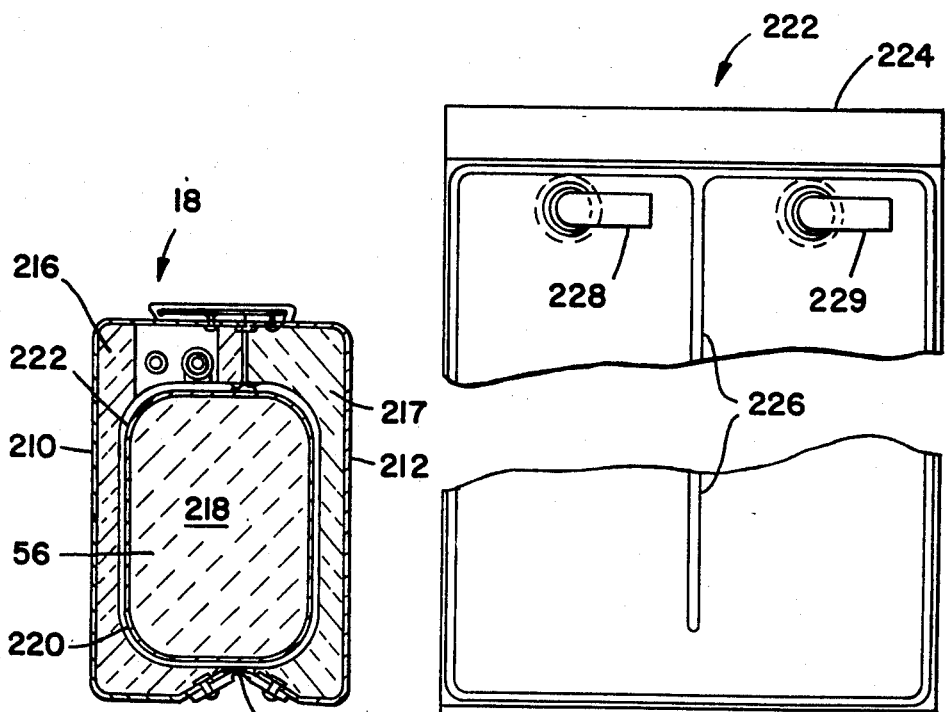
FIG_33
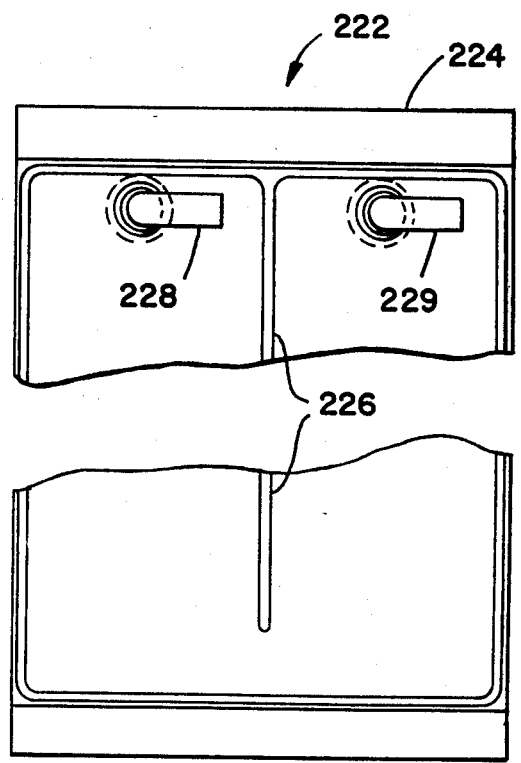
FIG_34

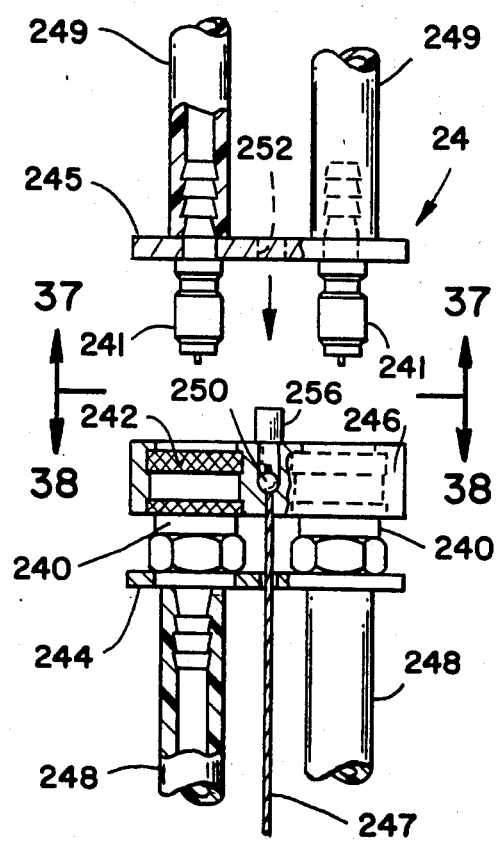
FIG _ 35
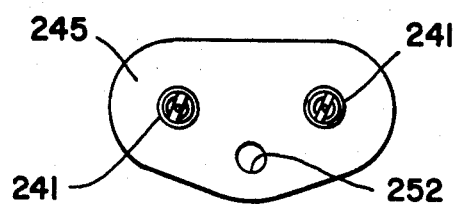
FIG _ 37
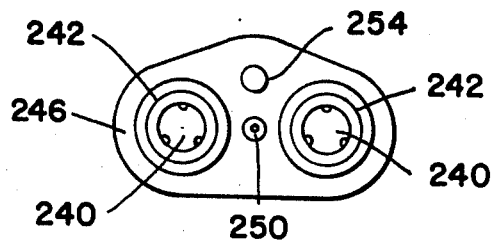
FIG _ 38
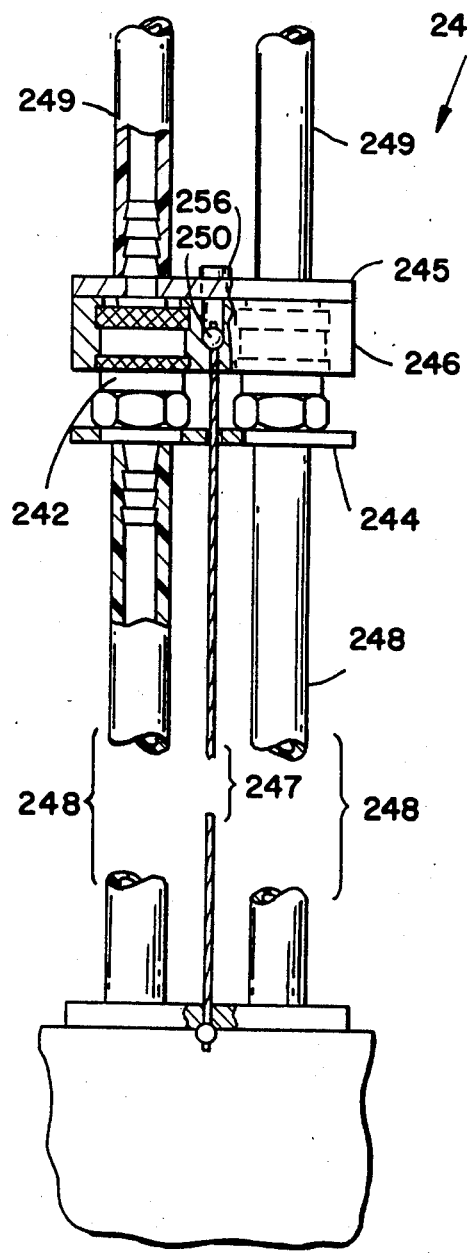
FIG _ 36

PERSONAL TEMPERATURE CONTROL SYSTEM

This application is a continuation of application Ser. No. 514,771, filed Apr. 1, 1983, now abandoned.

FIELD OF THE INVENTION

This invention relates to a personal temperature control system for enabling a person's body temperature to be controlled independently of the environment to which the person is exposed and more particularly to an improved liquid loop personal body temperature control system.

BACKGROUND OF THE INVENTION

In general, it is easier to protect a person from extremely low temperature environments than it is to protect a person from extremely high temperature environments. A person's body is a source of heat appropriately distributed by the person's circulatory system and thus, if the person's body is protected throughout against excessive heat loss to the environment, normal bodily functions can be maintained indefinitely.

From earliest recorded history, mankind has developed effective protective clothing for avoiding excessive heat loss to extremely cold environments by insulating the person's body from its environment. However, a person's body does not include any cooling source independent of its environment and thus mankind has not been as successful in developing protective clothing for avoiding excessive heating of a person's body in an extremely high temperature environment. For this reason, the preferred embodiments of this invention as shown in the drawing and described herein are specifically directed to the lowering of the temperature of a person's body below that which it would normally have in the environment to which it is exposed.

However, it will be understood that by simply providing the system of this invention with a source of heat rather than a source of cold, the temperature of a person's body could be raised to a temperature above that which it would normally have in any environment to which it is exposed. This might be done for therapeutic purposes in a normal environment, for example, as well as for maintaining normal body temperature in an extremely cold environment.

Three basic personal cooling systems have been proposed in the prior art. The first and least successful of these is to attempt to insulate the person's body from its environment by means of garments and then provide a source of cold within the garment such as blocks of ice, for example. Such a system is extremely uncomfortable for the user because of the great temperature differential between normal body temperature and the source of cold. In addition, the source of cold must be replenished at relatively short intervals requiring the opening of the garment and exposure of the person to the environment. Most importantly, such a system not only inactivates the normal cooling functions of the body through evaporation of perspiration but turns it into a disadvantage since the unevaporated perspiration will add to the discomfort of the user of such a system.

Thus, a second system was developed in the prior art based on attempts to augment the normal cooling functions of the body. One such approach is to place porous insulating garments in contact with the skin in an attempt to enhance the evaporation of perspiration and to augment the resulting cooling further by dampening the porous garment separately from perspiration. More sophisticated systems have included the circulation of air through the garment to enhance the evaporation and in some cases, the air has been cooled in an attempt to provide air conditioning as well as to enhance the evaporative cooling.

Again, such systems are extremely uncomfortable to the user since they tend to overpower the normal bodily functions of the user, producing unnatural conditions requiring excessive fluid intake by the user and discomfort at the skin and extremities, as well as loss of body fluids and salts.

More recently, liquid cooling loops have been proposed in which an attempt has been made to couple more directly to the normal circulatory system of a person's body. In such systems, heat exchange garments made of flexible material with liquid coolant passageways formed therein are placed in direct contact with the body of the user and liquid coolant is circulated through such garment. Insulating garments may be worn over the heat exchange garments and an attempt is made to cool the entire body of the user by circulating a cooled liquid through the liquid coolant passageways. Again, discomfort to the user has resulted from the tendency of such systems to overpower the normal cooling functions of the human body. The liquid coolant circulated is generally at a given temperature considerably below normal body temperature providing an excessive cooling effect in the extremities and a resultant upsetting of the normal circulatory system of the user. The upsetting of the normal functions of the circulatory system of the user may result in perspiration in parts of the body and excessive cooling at other parts of the body.

It is the principal object of applicant's invention to overcome the abovementioned disadvantages of the prior art by improved coupling of an external temperature source to the normal circulatory system of the user's body while preserving the normal bodily functions of the user and reducing the temperature differential between the user's body and the coolant.

SUMMARY OF THE INVENTION

A personal temperature control system according to applicant's invention comprises a first heat exchange device in the form of a garment adapted to be worn in contact with the skin of the user of the system including a body made of heat conductive material having an elongated fluid-tight passageway formed therein. According to preferred embodiments of the invention, such garments are worn only on the head and torso of the user. The system includes a second heat exchange device in the form of a body made of a heat conductive material having an elongated fluid-tight passageway formed therein, a reservoir containing fluid at atmospheric pressure and a fluid pump means having an inlet and an outlet. A first fluid conduit communicates the reservoir with the inlet of the pump means and a second fluid conduit communicates the outlet of the fluid pump means to one end of the elongated fluid passageway formed in the body of one of the heat exchange devices. A third fluid conduit means communicates the other end of the elongated fluid passageway in the body of one of said heat exchange devices with one end of the elongated fluid passageway formed in the body of the other of the heat exchange devices. A fourth fluid conduit means communicates the other end of the elongated fluid passageway formed in the body of such other of the heat exchange devices with the reservoir and an adjustable flow valve means communicates between the ends of the elongated fluid passageway formed in the body of the second heat exchange device. A temperature source independent of the body of the user is placed in heat exchange relation to the second heat exchange device.

BRIEF DESCRIPTION OF THE DRAWING

This invention wll be more fully understood from a reading of the following detailed description of preferred embodiments thereof with reference to the appended drawing wherein:

FIGS. 1A through 1F are perspective views of various preferred embodiments of applicant's improved personal temperature control system as applied to the body of a user;

FIGS. 2A and 2B are schematic diagrams showing the coolant flow in alternate preferred embodiments of applicant's personal temperature control system;

FIG. 3 is a plan view of a head-engaging garment suitable for use in applicant's improved personal temperature control system, showing the coolant passageways formed therein;

FIG. 4 is a fragmentary plan view of a torso engaging garment suitable for use in applicant's improved personal temperature control system showing the fluid passageways therein;

FIG. 5 is a cross-sectional view showing the first step in the attachment of an inlet or outlet coupling elbow to a garment according to applicant's improved personal temperature control system;

FIG. 6 is a cross-sectional view showing the second step in the attachment of an inlet or outlet coupling elbow to a garment according to applicant's improved personal temperature control system;

FIG. 7 is a right side view in elevation of a head-engaging garment according to a preferred embodiment of applicant's improved personal temperature control system.

FIG. 8 is a left side view in elevation of the head-engaging garment of FIG. 7 mounted inside a helmet represented in phantom;

FIG. 9 is a rear view in elevation of the head-engaging garment of FIG. 7;

FIG. 10 is a cross-sectional view taken along lines 10—10 of FIG. 9;

FIG. 11 is a perspective view showing the torso engaging surface of a garment in accordance with applicant's improved personal temperature control system;

FIG. 12 is a perspective view of the exterior surface of the torso engaging garment according to applicant's improved personal temperature control system;

FIG. 13 is a perspective view taken from one side of a support harness suitable for use in a preferred embodiment of applicant's improved personal temperature control system;

FIG. 14 is a perspective view taken from the opposite side of the support harness of FIG. 13;

FIG. 15 is a perspective view of the control display unit according to the preferred embodiment of applicant's improved personal temperature control system;

FIG. 16 is a view taken along line 16—16 of FIG. 15 with the battery pack and control cover removed;

FIG. 17 is a cross-sectional view of the control cover and reservoir taken along line 17—17 of FIG. 15;

FIG. 18 is a cross-sectional view taken along line 18—18 of FIG. 15;

FIG. 19 is a cross-sectional view taken along line 19—19 of FIG. 17 showing the internal fluid coolant flow passageways of the control display unit of FIG. 15;

FIG. 20 is a top plan view of the control display unit of FIG. 15;

FIG. 21 is a cross-sectional view taken along line 21 of FIG. 20;

FIG. 22 is an enlarged fragmentary exploded, partially cross-sectional view taken along lines 22 of FIG. 19 showing the adjustable flow valve means according to applicant's improved personal temperature control system;

FIG. 23 is an enlarged side view in elevation of the active valve element of the adjustable flow valve means of FIG. 22;

FIG. 24 is a left end view in elevation of FIG. 23;

FIG. 25 is a right end view in elevation of FIG. 23;

FIG. 26 is a further enlarged cross-sectional view taken along lines 26—26 of the valve element of FIG. 23 with a fragmentary cross-sectional showing of the fluid passageway in which it is mounted according to the preferred embodiment of the improved personal temperature control system of applicant's invention;

FIG. 27 is a graph showing the variation in liquid coolant flow through the second heat exchange device of the personal temperature control system of applicant's invention in relation to the rotation of the valve element of FIG. 23;

FIG. 28 is a graph showing the variation in temperature of the liquid coolant in the body-engaging garment in relation to the rotation of the adjustable flow valve means according to the preferred embodiment of applicant's improved personal temperature control system;

FIG. 29 is a perspective view of the second heat exchange device according to a preferred embodiment of applicant's improved personal temperature control system;

FIG. 30 is a cross-sectional view taken along line 30—30 of FIG. 29;

FIG. 31 is a cross-sectional view similar to FIG. 30 with portions broken away to show the heat exchange structure;

FIG. 32 is a perspective view similar to FIG. 29 but with the cover of the second heat exchange device shown in open position with a frozen can of coolant indicated in phantom;

FIG. 33 is a cross-sectional view taken along line 33—33 of FIG. 32;

FIG. 34 is a plan view of the heat exchange structure of the second heat exchange device when removed from its case;

FIG. 35 is an exploded side view in elevation of a quick disconnect coupling according to the preferred embodiment of applicant's improved personal temperature control system with portions broken away to show the internal structure thereof;

FIG. 36 is a side view in elevation of the quick disconnect coupling of FIG. 35 shown in operative engagement partially broken away to show the internal structure thereof and the remote end thereof;

FIG. 37 is an end view in elevation taken along lines 37—37 of FIG. 35; and

FIG. 38 is an end view in elevation taken along line 38—38 of FIG. 35.

DETAILED DESCRIPTION OF PREFERRED EMBODIMENTS

Referring to FIG. 1A of the drawing, it is a basic object of applicant's invention to provide an intimate coupling to the normal circulatory system of a person's body. To this end applicant provides a heat exchange garment 10 in the form of a helmet 12 intimately coupled to the head of the user and a vest 14 intimately coupled to the torso of the user. The torso of the body comprises a large portion of the surface area of the body housing the center of the circulatory system and is relatively immobile as compared to the extremities of the body thus enhancing intimate and continuous coupling to the circulatory system. Similarly, the head of the body provides a substantial relatively immobile surface area and one in which the normal body circulation is relatively constant regardless of temperature fluctuations. Thus, it is a basic premise of applicant's invention that if sufficient coupling is made to the head and torso of the body of the user of applicant's system to maintain the normal temperature range of the head and torso regardless of the ambient temperature to which the body is exposed, the normal circulatory system of the body will tend to maintain normal body temperature in its extremities. Although not shown in FIGS. 1A through 1F, it is desirable to provide suitable protective clothing over the temperature control system, including the extremities of the body to avoid excessive temperature interchange with the environment.

As shown in FIGS. 1B through 1E, one preferred embodiment of this invention would be fully self-contained and mobile although as shown in FIG. 1F, applicant's system could also be used with a fixed temperature source. Thus, as shown in FIGS. 1B and 1C, a support harness 16 may be worn by the user over the vest-like portion of the heat exchanger 10 which is in intimate contact with the skin of the user.

As shown in FIG. 1C, a heat exchange device 18 containing a temperature source in accordance with the teaching of this invention may be removably mounted on the support harness 16. Similarly, a control display unit 20 including a fluid pump and a reservoir means in accordance with the teaching of this invention, may be removably mounted on the support vest 16. The heat exchange device 18 is connected to the heat exchange garment 10 through the control display device 20 and an umbilical cord 21 containing the necessary fluid conduits. Alternatively, as shown in FIG. 1D, the heat exchange device 18 and control display unit 20 could be mounted on a belt worn about the waist of the user.

As shown in FIG. 1E, the heat exchange device 18 and control display unit 20 could be mounted on an appropriate hand carrier 22 adapted to be received on a mounting bracket 23 which may be fixed in position adjacent the normal work position of the user. Finally, as shown in FIG. 1F, a modified control display unit 20' may be permanently mounted to a fixed heat exchange device capable of supplying cooled fluid for a number of systems according to the teaching of this invention as will be more fully described hereinafter. Where the heat exchange device 18 and control display unit 20 are hand carried as shown in FIG. 1E, or where the control display unit 20' is rigidly mounted to a fixed heat exchange device shown in FIG. 1F, the umbilical cord 21 is connected to the control display units 20 and 20' by means of an automatic quick release coupling 24 in accordance with the teaching of this invention, as will be more fully described hereinafter.

Referring to FIG. 2A, the control display unit 20 according to this invention, comprises a pump 26 and reservoir 28 contained within a housing 30. The inlet of the pump 26 communicates with the reservoir 28 through a filter 32 within the housing 30. The pump 26 is driven by an electrical motor 34 which is mounted within the housing 30. The motor 34 is powered by a battery 36 which may be removably mounted to the exterior of the housing 30 and electrically connected to the motor through a switch 38 mounted on the housing 30.

The outlet of the pump 36 is connected to a first quick disconnect coupling 40 mounted on the housing 30. The umbilical cord 21 includes a first conduit adapted to be connected to the coupling 40 and conduct a flow of fluids therefrom to the heat exchange garment 10 and a second conduit adapted to return fluid flow from the heat exchange garment 10 to a second quick disconnect coupling 42 mounted on the housing 30. The second quick disconnect coupling 42 communicates with a flow restrictor 44 within the housing 30 which in turn communicates with a flow meter 46 mounted on the housing 30 for visual observation. The output of the flow meter 46 communicates with both a third quick disconnect coupling 48 and the inlet of an adjustable flow valve means 50. The outlet of the adjustable flow valve means 50 communicates with the reservoir 28.

The quick disconnect coupling 48 is coupled through an appropriate conduit to the heat exchange device 18 and a fourth quick disconnect coupling 52 mounted on the housing 30 communicates with the reservoir 28. An appropriate conduit returns fluid flow from the heat exchange device 18 to the fourth quick disconnect coupling 52. As indicated at 54, the reservoir 28 is open to atmospheric pressure preferably by making the walls thereof flexible in order to avoid the necessity of a vent which might allow leakage of fluid from the system.

It wll be seen that the adjustable flow valve means effectively communicates between the third 48, and fourth 52 couplings. Thus, when the adjustable flow valve means 50 is fully open, little if any fluid will flow to the coupling 48 for communication to the heat exchange device 18. When the adjustable flow valve means 50 is fully closed, all fluid flow in the system will pass through the coupling 48 and into the heat exchange device 18, returning to the reservoir 28 through the coupling 52. Thus, the proper setting of the adjustable flow valve means 50 will insure the minimum flow of fluid to the heat exchange device 18 required to maintain the desired temperature of the fluid flow in the heat exchange garment 10. It is an important object of this invention to maintain the temperature of the fluid flow in the heat exchange garment 10 as near normal body surface temperature as posible through circulation of the minimum fluid flow in the heat exchanger means 18. This not only insures maximum comfort of the user of the system, but will also conserve the temperature source 56 in the heat exchange device 18.

The pump 26 and flow restrictor device 44 are selected to maintain a fluid pressure of ten to fifteen pounds per square inch gauge in the heat exchange garment 10 in order to resist external forces imposed thereon which may tend to obstruct the elongated passageways formed therein for the circulation of fluid. At the same time, the flow restrictor means 44 reduces the fluid pressure to which the heat exchange device 18 is subjected to a maximum of two to four pounds per square inch gauge in order to avoid unnecessary pressures in the heat exchange unit which may result in leakage or rupture in the heat exchange unit.

In the embodiment of this invention shown in FIG. 2A, the temperature source 56 preferably comprises a separate body from the heat exchanger 18, such as a block of ice within an appropriate container, for example. As will be described more fully hereinafter, the heat exchanger 18 according to this invention, is designed to enable convenient removal and replacement of the temperature source 56 in intimate heat exchange relation with the heat exchanger 18.

As shown in dotted lines in FIG. 2A, two or more heat exchangers 18 together with associated temperature sources 56 may be used in series in order to increase the capacity of the system. The use of two or more heat exchangers 18 in series enables a given temperature in the heat exchange garment 10 to be maintained at a reduced flow through the heat exchangers 18 established by an appropriate setting of the adjustable flow valve 50. Such reduced flow together with the increased volume of the temperature source 56 will enable the desired temperature to be maintained in the heat exchange garment 10 for a longer period of time. Alternatively, a greater temperature differential may be established between the heat exchange garment 10 and the environment in which it is used at a given rate of flow through the series connected heat exchangers 18.

Referring to FIG. 2B, an alternate embodiment of the personal temperature control system according to the teaching of this invention is shown which is suitable for use with a substantially immobile high capacity heat exchanger 58 coupled to a continuously circulating temperature source 60. The embodiment of FIG. 2B is constructed of the same components as the embodiment of FIG. 2A but such components are arranged in a different way. For clarity and ease of understanding, the same reference numerals have been used in FIG. 2B to identify corresponding components. Thus, in the embodiment of FIG. 2B a motor 34 powered by a battery 36 through a switch 38, drives a pump 26. The inlet of the pump 26 communicates with the reservoir 28 through a filter 32. However, the outlet of the pump 26 in the embodiment of FIG. 2B is connected to the coupling 48 which communicates with the inlet of the heat exchanger 58. The outlet of the heat exchanger 58 communicates with the coupling 52 which in turn communicates with the coupling 40 through the flow meter 46. The coupling 40 communicates with the inlet of the heat exchange garment 10 and the outlet of the heat exchange garment 10 communicates with the coupling 42. The coupling 42 communicates with the reservoir 28 through a flow restrictor device 44. The adjustable flow valve 50 effectively communicates between the coupling 48 and the coupling 52, thereby enabling the flow through the heat exchanger 58 to be controlled at substantially constant pressure. The restrictor device 44 enables the desired pressure to be maintained within the heat exchange garment 10 although the reservoir 28 is maintained at atmospheric pressure as indicated at 54.

As indicated in FIG. 2B, a plurality of personal temperature control systems each utilized by a different individual may be connected in parallel to the heat exchanger 58. The heat exchanger 58 may be any conventional liquid loop heat exchanger with a liquid loop temperature source 60 including an appropriate accumulator 62 to provide additional volume at constant pressure in the liquid loop in order to accommodate the attachment and removal of parallel temperature control systems. It will be understood that the parallel personal temperature control systems will function independently of each other to allow each user to regulate the temperature maintained in the heat exchange garment 10 associated therewith as required.

It is a basic principle of the personal temperature control system according to applicant's invention to maintain a constant high level of liquid flow through the heat exchange garment 10 at a temperature as near as possible to normal body temperature while providing the necessary heat exchange between the circulatory system of the body and the liquid loop of the heat exchange garment 10. A large temperature differential between the blood in the circulatory system and the liquid in the heat exchange garment 10 will, of course, tend to provide high thermal exchange therebetween. However, not only will a large temperature differential between the blood in the circulatory system and the liquid in the heat exchange garment 10 tend to make the garment 10 uncomfortable in use, but it will actually decrease the thermal coupling by causing constriction of the blood vessels in the body of the user. Thus, according to applicant's invention, the minimum amount of liquid cooled in the heat exchanger 18, 58 is mixed with liquid from the outlet of the heat exchange garment 10 to produce a liquid temperature of 50°–70° F. at the inlet of the heat exchange garment 10. In the preferred embodiment of applicant's invention as shown in the drawing, the liquid is first introduced into the helmet portion 12 of the heat exchange garment 10 and then to the vest portion 14 of the heat exchange garment 10. The head is widely recognized as an important area for heat exchange between man and environment. The relatively small amount of vaso-constriction which occurs in the head under conditions of thermal stress provides good thermal coupling even where relatively high temperature differentials are involved. It has been found that although the head only comprises 2%–3% of the total area of the body, it provides a much larger percentage of the actual heat exchange between the body and the environment and in terms of personal comfort and psychological effects, is weighted at 20%–40% of the overall factors. For example, in controlling a person's temperature in a high temperature environment, it has been found that the head may be subjected to temperatures between 50°–60° F. without reducing thermal coupling due to vaso constriction or contributing to the discomfort of the user. On the other hand, in similar situations, temperature below 70° F., will result in serious vaso constriction in the torso of the body. Thus, according to applicant's invention, when used in such a situation, liquid having a temperature between 50°–60° F. is first introduced to the helmet 12 of the heat exchange garment 10 where the thermal coupling will result in liquid leaving the helmet at a temperature approaching 70° F. Such liquid is then introduced to the vest 14 of the heat exchange garment 10 in order to maintain good thermal coupling by avoiding vaso-constrictions in the torso of the user.

As shown in FIG. 2A, the mixing of the warm liquid from the heat exchange garment 10 with the cooled liquid from the heat exchanger 18 occurs in the reservoir 28. The relative amounts of the warm liquid from the heat exchange garment 10 and the cooled liquid from the heat exchanger 18 is regulated by the adjustable flow valve 50 in order to provide a liquid in the reservoir 28 having the desired temperature for introduction to the heat exchange garment 10 through the pump 26. In the embodiment of this invention shown in FIG. 2B, the mixing of the warm liquid from the heat exchange garment 10 with cooled liquid from the heat exchanger 58 occurs in the conduit through which the mixture is introduced to the heat exchange garment 10. Again, the adjustable flow valve 50 regulates the relative amounts of the warmed liquid and cooled liquid to provide the desired liquid temperature at the inlet to the heat exchange garment 10.

Referring to FIGS. 3 and 4, the helmet portion 12 and the vest portion 14 of the heat exchange garment 10 may be fabricated in accordance with the processes disclosed in applicant's prior U.S. Pat. No. 3,830,676, the teaching of which is incorporated herein by reference. However, according to the teaching of this invention, the helment portion 12 and vest portion 14 of the heat exchange garment 10 are each preferably made of two overlying sheets of nylon fabric having a urethane coating on their adjacent surfaces. According to the preferred embodiment of this invention, the two sheets comprising the helmet portion 12 of the heat exchange garment 10 are cut to the contour indicated by the dot-dash line 62 in FIG. 3. Such contour includes lobes 64 for engaging the neck of the user, lobes 65 for engaging the cranium and temples of the user, and intermediate lobes 66 for engaging the back of the head of the user. the overlying contoured sheets are pressed between a flat plate and a die member having lands formed in the abutting surface thereof, as indicated by the solid lines, defining channels therebetween. Either, or both, of the die member and the plate may be heated so that the abutting urethane coatings on the two sheets are bonded together under the lands to define the desired liquid coolant channels between the sheets.

According to the preferred embodiment of this invention, as shown in FIG. 3, an elongated outlet channel 67 extending from one end of the contour 62 to the other between the lobes 64, 65 and 66 is provided. The channel 67 is closed at its end in the nape lobes 64 and open at its end in the cranium lobes 65. An inlet channel 68 is provided at the free end of the nape lobe 64 communicating therewith. Thus, liquid introduced into the inlet channel 68 at the nape lobe 64 end thereof will be communicated through the channels in the nape lobes 64 in parallel, the channels in intermediate lobes 66 in parallel, and to the cranium lobes 65, where it will flow through the channels thereof in parallel to the free end of the outlet channel 67.

Referring to FIG. 4, the vest portion 14 of the heat exchange garment 10 according to the preferred embodiment of this invention, comprises mirror image front and back portions joined at one side. Only one of the panels and the side connection is shown in FIG. 4. As described hereinabove in connection with the helmet portion 12, two sheets of nylon fabric having a urethane coating on one side thereof are cut to the contour indicated by dot-dash lines 70 in FIG. 4. The contoured sheets are arranged in overlying relation with their urethane coatings in abutment. The sheets are then pressed between a flat plate and a die member having lands thereon as indicated in solid lines in FIG. 4 to form channels for liquid coolant flow as described hereinabove. According to the preferred embodiment of this invention, such channels extend generally horizontally across the front and back panels and are arranged in upper and lower groups of channels.

An inlet channel 72 is formed in the interconnecting side of the vest 14 between the front and back panels. The inlet channel 72 communicates with the upper array of channels and an interconnecting channel 74 at the free side of each panel connects the upper array of channels with the lower array of channels. The lower array of channels communicate with an outlet channel 76 formed in the interconnecting side of the vest 14. Thus, liquid flows into the vest 14 and across the top portion thereof, returning across the lower portion thereof, thereby contributing to the comfort of the garment, since liquid having the minimum difference in temperature from the temperature of the blood in the circulatory system of the user, will be presented to the sensitive stomach and back area of the user, the shoulders and chest of the user being generally less sensitive.

According to this invention, liquid is coupled into the inlet channels 68 and 72 of the helmet 12 and vest 14 and out of the outlet channels 67 and 76 of the helmet 12 and vest 14 by means of coupling elbows 80 having a flange 82 at one end thereof as best shown in FIGS. 5 and 6. The location of the elbow couplings 80 are indicated in dotted lines in FIGS. 3 and 4, and the method of attaching such couplings according to the teaching of this invention, is shown in FIGS. 5 and 6.

Thus, as shown in FIG. 5, one of the two sheets of the helmet 12 and one of the two sheets of the vest 14 is punched to provide holes therethrough in the appropriate locations to communicate with the inlet 68, 72 and outlet 67, 76 channels thereof, respectively. The elbow couplings 80 are then fixed to the sheet having the holes formed therein prior to its being placed in overlying relationship to the other sheet. The elbow coupling 80 is passed through the hole and its flange brought into contact with the urethane coated side of the nylon fabric. As shown in FIG. 5, the flange 82 is then pressed against the urethane coating under heat and pressure to form a liquid-tight seal between such flange 62 and the sheet about the hole.

As shown in FIGS. 3, 4 and 6, the elbows 80 are oriented so that they will be in alignment with the respective inlet 68, 72 and outlet 67, 76 channels to be formed. As best shown in FIG. 6, the dimensions of the flange 82 are larger than the transverse dimensions of the respective channels 67, 68, 72, 76 and appropriate pockets are formed in the flat plate to accommodate the coupling elbows 80 during the pressing of the sheets to form the liquid channels therebetween. As a result, the sides of the respective inlet 68, 72 and outlet 67, 76 channels will be sealed to the flange 82 of the respective elbows 80 but no seal will be formed directly over such channels 67, 68, 72, 76. This arrangement will prevent "ballooning" from occurring between the sheets of the helmet 12 and vest 14 at the inlet and outlet elbows 80 thereof.

Referring to FIGS. 7 through 10, the helment portion 12 of the heat exchange garment 10 according to this invention, may preferably include an insulating covering 86. As best shown in FIG. 10, the two sheets having the contour 62 shown in FIG. 3, and sealed together to provide for liquid transport, are mounted within the insulating covering 86. The dimensions of the contour 62 are selected to accommodate the full range of human head sizes and similarly, the insulating covering 86 is shaped to accommodate the full range of human head sizes from the cranium to the nape of the neck. The cranium engaging portions of the contoured sheets 62 and of the insulating covering 86 are fixed to each other and an elastic means 88 at the nape portion of the insulating covering 86 engages one or both elbow couplings 80. Thus, when the insulating covering 86 is applied to the head of the user, the liquid transport means will be held against the head of the user with differences in size being accommodated by the elastic means 88.

The insulating covering 86 may be provided with a chin strap 90 to facilitate the snug fit of the helmet 12 to the head. In addition, the protective covering 86 may be provided with external tab fasteners 92 to enable the mounting of the helmet 12 within a rigid outer protective helmet 94. The tabs 92, as well as the chin strap 90 may be provided with fastening means 96, 97 of the type sold under the trademark VELCRO, for example, in order to enable quick and effective adjustment of the helmet 12 to the head and the outer protective helmet 94.

Referring to FIG. 11, the vest portion 14 of the heat exchange garment 10 may also comprise an external insulating cover 102 having a vest-like conformation comprising front and back panels joined at one side with the liquid transport means fixed to its inner surface, as indicated by dotted lines, for contact with the skin of the torso of the user. As shown in FIG. 12, the umbilical cord through which the liquid inlet and outlet conduits pass, is fixed to the outer surface of the vest-like insulating cover 102 at the interconnected side of the panels. It is an important feature of this invention that the interconnection between the panels of the vest 14 may be located at either the left side or the right side of the user. For this reason, the free end of the umbilical cord 21 is provided with a fastening means 104 of the type sold under the trademark VELCRO. The fastening means 104 enables the free end of the umbilical cord to be shifted from one panel to the other of the vest 14 so that it will be located at the back of the vest regardless of whether the interconnected sides are at the right or at the left of the user.

In order to provide for easy adjustment of the vest to accommodate users of various sizes, the fastening means for closing the open side of the vest is preferably of the type commercially available under the trademark VELCRO. Thus, as shown in FIGS. 11 and 12, identical fastening pads 106 are provided on the exterior surface of both panels at the free sides thereof together with a zipper means 107. A fastening strap 108 is adapted to be attached to either side by the zipper means depending on whether the interconnected sides of the panels are to be located at the left or at the right of the user.

Similarly, a pair of shoulder straps 110 are provided having snap type fasteners 112 at one end, one of the elements 114 of the type of fastener commercially available under the trademark VELCRO at the other end. Two cooperating snap type fasteners 113 and two cooperating elements 115 of the type of fastener commercially available under the trademark VELCRO are provided at the upper edges of each panel, as best shown in FIG. 12 in order to provide reversibility of the shoulder straps 110. Thus, in use, the fasteners 114, 115 may always be oriented to the front of the user to facilitate quick adjustment by the user.

Referring to FIGS. 13 and 14, the support harness 16 of FIGS. 1B and 1C is shown in detail. The support harness 16 includes a support panel 120 the exterior surface of which is shown in FIG. 13 and the interior or body facing surface of which is shown in FIG. 14. The support panel 120 is provided with a plurality of snap type fasteners arranged in three arrays of four each for mounting the components of a personal temperature control system according to this invention. Thus, the first array 121 of four snap type fasteners is adapted to mount the control display unit 20 of the personal temperature control system to the support panel 120. A second array 122 of four snap type fasteners is adapted to mount the heat exchange device 18 to the support panel 120. Similarly, a third array of four snap type fasteners is adapted to mount a second heat exchange device 18 to the support panel 120 if required.

The support harness 16 is provided with adjustable length shoulder straps 124 and an adjustable length belt 126 having a quick release buckle. The support harness may be worn with the support panel 120 thereof either on the front or the back of the user and to facilitate such reversibility, a cross strap 128 having a quick release buckle interconnects the shoulder straps 124 as best shown in FIG. 14. Conventional clothing may be interposed between the support harness 16 and the vest portion 14 of the heat exchange garment 10 as desired.

Referring to FIG. 15, a perspective view of the control display unit 20 according to the preferred embodiment of this invention is shown together with a battery pack 36. For purposes of clarity and ease of understanding, the same reference numerals used in FIGS. 2A and 2B will be used in FIG. 15 together with FIGS. 16 through 26 to identify corresponding components. Thus, the housing 30 of the control display unit 20 comprises a hollow cup-like body of generally rectangular cross-section closed at the top by a control plate 130. The conduits interconnecting the various components of the control display unit 20 are formed in the cover plate 130 and communicate with the quick disconnect couplings 40, 42, 48 and 52, which couplings are carried by the control plate 130.

Referring to FIG. 16, a right end view of the housing of FIG. 15 is shown with the cover plate 130 and battery pack 36 removed. Snap-type terminals 132 adapted to cooperate with corresponding snap-type terminals on the battery pack 36 for electrical connection purposes are shown as mounted through the housing 30. Similarly, male snap-type mounting pins 134 are shown mounted on the rear side of the housing 30 which are adapted to cooperate with corresponding snap elements on the support harness to enable the control display unit 20 to be carried thereby. A battery pack mounting plate 135 is shown fixed to the end of the housing 30 and adapted to cooperate with battery pack mounting clamp 136 to mount the battery pack 36 to the housing 30 with its terminals in engagement with the snap-type battery terminals 132.

As best shown in FIGS. 15, 17, 18 and 21, a flexible rubber boot 138 projects from the upper surface of the control plate 130 and surrounds the actuating button of the control switch 38 which is carried by the control plate 130. Thus, downward pressure on the rubber boot 138 exerted by the thumb or finger of the user will actuate the control switch 38 to turn the control display unit on or off.

As best shown in FIG. 19, the control plate 130 is provided with a plurality of bores and passageways defining mounting cavities and conduits for the various components of the control display unit 20. Thus, a first passageway 140 extending in the plane of the control plate 130 terminates in communication with a passageway 141 extending transversely to the plane of the control plate 130 providing an opening in the bottom of the control plate 130. The open end of the passageway 140 is threaded to receive the first quick disconnect coupling 40. The opening of the transverse passageway 141 is adapted to communicate with the outlet of the pump 26. Similarly, a second passageway 142 is threaded at its open end to receive the second quick disconnect coupling 42. The passageway 142 communicates with a passageway of reduced cross-section 144 through the orifice of the flow restrictor device 44 of the preferred embodiment of this invention which is mounted in the passageway 142.

The passageway 144 communicates with a cavity 146 in the upper surface of control plate 130 in which is mounted the flow meter 46 according to the preferred embodiment of this invention. A third passageway 148 extending in the plane of the control plate 130 is threaded at its open end to receive the third quick disconnect coupling 48 and extends into communication with the cavity 146 to provide the outlet for the flow meter 46.

As will be described more fully hereinafter, the adjustable flow valve 50 is mounted in a cavity 149 formed in the upper surface of control plate 130 with the valving element 150 projecting from the upper surface thereof. A control knob 151 is mounted on the projecting end of the valving element 150.

A fourth passageway 152 extending in the plane of the control plate 130 is threaded at its open end to receive the fourth quick disconnect coupling 52. An interconnecting passageway 153 extending in the plane of the control plate 130 transversely to the third 148 and fourth 152 passageways, intersects the cavity 149 in which the valve element 150 of the adjustable flow valve 50 is mounted and communicates between the third 148 and fourth 152 passageways. A passageway 154 extends transversely of the plane of the control plate 130 from an opening in the bottom surface thereof into communication with the junction between the fourth passageway 152 and the interconnecting passageway 153 providing an outlet from such passageways into the reservoir 28.

A second passageway 155 extending from an opening in the underside of the control plate 130 in communication with the reservoir 28 transversely of the plane of the control plate 130 partway therethrough is provided and serves as a socket for receiving one end of an extraction tube 156 which projects into the reservoir 28 to enable extraction of liquid therefrom. Similarly, a further passageway 157 extends from an opening in communication with the reservoir 28 transversely of the control plate 130 all the way therethrough to enable liquid to be introduced into the reservoir to supplement the liquid in the system. A second interconnecting passageway 160 extending in the plane of the control plate 130 generally parallel to the passageways 140 and 144 communicates with the passageway 155 and through the opening thereof with the reservoir 28. The end 162 of the passageway 160 remote from the passageway 155 and adjacent the passageway 140, is enlarged to receive a filter element and extends to a threaded opening 164 at the end of the control plate 130. The threaded opening 164 is adapted to receive a threaded plug and thereby enables the filter element contained in the end 162 of the passageway 160 to be replaced as required in operation.

A passageway 166 extending transversely of the plane of the control plate 130 from an opening in the underside thereof extends into communication with the end 162 of the passageway 160 to receive liquid from the reservoir 28 which passes through the filter element 32. The passageway 166 serves as the inlet to the pump 26 and the transverse passageway 141 communicating with the passageway 140 serves as the outlet from the pump 26. As best shown in FIG. 18, the pump 26 is mounted against the underside of the control plate 130 as by means of mounting screws 168, for example (FIG. 20), with its inlet and outlet in sealed communication with the passageways 166 and 140, respectively.

Referring to FIGS. 17 and 20, the upper end of the passageway 157 may be threaded to receive a threaded plug 170 which may be removed as required to fill the reservoir 28 and then replaced to seal the system against leakage of liquid. Finally, as shown in FIGS. 19 and 21, a cavity 172 in the undersurface of the control plate 130 including an opening 173 extending through the upper surface of the control plate 130 is provided for mounting the switch 38.

As best shown in FIGS. 20 and 21, the flow meter 26 comprises a vaned rotor 176 mounted for rotation on a vertical axle 177 within the cavity 146. The cavity 146 opens through the upper surface of the control plate 130 and is closed by a transparent cap 178 through which the rotor 176 may be viewed. Liquid flowing through the passageway 144 into the cavity 146 and out of the cavity 146 into the passageway 148 will cause the vaned rotor 176 to rotate about the axle 177 at a speed related to the volume of liquid flow. Thus the flow meter 26 provides the user of the system with a visual indication of the operating condition of the system.

Referring again to FIGS. 17 and 18, the reservoir 28 in the preferred embodiment of this invention comprises a hollow, thin-walled, generally rectangular, body of a flexible plastic material, for example impervious to the liquid in the system. The reservoir 28 is fully sealed except for three nipple-like openings in one end wall thereof, each adapted to be sealingly received in a different one of the openings of the passageways 154, 155 and 157. Thus, when the reservoir 28 is mounted on the control plate 130 for operation with appropriate connections made to the quick disconnect couplings 40, 42 and 52, and the fill plug 170 in place, the reservoir 28 will be fully sealed. However, the flexing of the flexible walls of the reservoir 28 will maintain the liquid within the reservoir at atmospheric pressure thereby eliminating any need for a vent that might result in leakage of liquid from the system.

As shown in FIG. 18, the reservoir 28 is dimensioned to occupy about half the volume of the housing 30. A thermal insulating cup 180 is mounted within the housing 30 and dimensioned to receive the reservoir 28 with a loose fit. The pump 26 and the drive motor 34 are contained in the balance of the volume of the housing 30.

Referring to FIGS. 22 through 28, the structural and operational details of the adjustable flow valve 50 according to the preferred embodiment of this invention are shown. According to the teaching of this invention, the adjustable flow valve means 50 is interposed in a conduit communicating between the inlet and the outlet of the heat exchange device 18. Thus, when the adjustable flow valve 50 is fully closed, all of the liquid flow in the system will pass through the heat exchange device 18 and when the valve 50 is fully open, little if any of the liquid will flow through the heat exchange device 18. However, under conditions of maximum liquid flow through the heat exchange device 18, the temperature differential between the liquid entering the heat exchange device and the liquid exiting from the heat exchange device 18 will be less than the temperature differential between the entering and leaving liquid under minimum flow conditions. This is due to the fact that under low flow conditions, the liquid will tend to remain in the heat exchanger 18 for a longer period of time than under high flow conditions. For this reason, intermediate flow rates through the heat exchange device 18 will tend to be relatively ineffectual in achieving personal temperature control. According to the preferred embodiment of this invention, the adjustable flow valve means 50 is designed to provide a non-linear change in flow rate therethrough in response to the adjustment thereof in order to provide effective intermediate settings.

Thus, referring to FIGS. 22 through 25, it will be seen that the adjustable flow valve 50 according to the preferred embodiment of this invention comprises a cavity 149 in the form of a truncated right circular cone tapering from maximum cross-sectional dimensions at the opening thereof in the upper surface of the control plate 130 to minimum cross-sectional dimensions at the bottom. The interconnecting channel 153 intersects the cavity 149 tangentially intermediate the open top and closed bottom thereof. The cross-sectional diameter of the passageway 153 is substantially equal to the radius of the cavity 149 in the cross-sectional plane of the cavity 149 passing through the center of the passageway 153 and the depth of the cavity 149 is, of course, larger than the cross-sectional diameter of the passageway 153.

A valve element 150 of the adjustable flow valve 50 according to the preferred emodiment of this invention comprises a plug portion 182 having the general shape of a truncated right circular cone dimensioned to snugly fit into the cavity 149. A right circular cylindrical shaft portion 184 coaxial with the plug portion 182 projects integrally from the base of the plug portion 182 and is provided with a flat 185 for the removable mounting of the control knob 151 thereon. The cross-sectional diameter of the shaft portion 184 is smaller than the cross-sectional diameter of the base of the plug portion 182 thus providing a shoulder 186 (see FIG. 23) that may be engaged by a mounting plate 187. The mounting plate 187 may be fixed to the upper surface of the control plate 130 by means of screws, for example, as indicated by the threaded holes 188 in the control plate 130 and apertures 189 through the mounting plate 187 to hold the plug portion 182 of the valve element 150 in the cavity 149.

A groove 190 is formed about the periphery of the plug portion 182 adjacent its base and a resilient sealing washer or O-ring 192 is received in the groove 190 (see FIG. 23). The O-ring 192 is dimensioned to sealingly engage the interior surface of the cavity 149 to prevent the escape of liquid when the plug portion 182 is held in place in the cavity 149 by the mounting plate 187.

The exterior side surface of the plug portion 182 of the valve element 150 is relieved intermediate the base and truncated end of the plug portion 182 to provide a valving surface 194. The valving surface 194 is dimensioned and located to be brought into alignment with the passageway 153 when the plug portion 182 of the valve element 150 is fully received in the cavity 149.

Referring to FIG. 26, the valve element 150 is shown in cross-section as fully received in the cavity 149 with its valving surface 194 in position to fully block the flow of liquid indicated by the arrows 196 in the channel 153. According to the preferred embodiment of this invention as shown in FIG. 26, the valving surface 194 of the valve element 150 is designed so that rotation of the valve element 150 in the direction indicated by the arrow 198 in FIG. 26 through an arc of about 120° will fully open the passageway 153 to the flow of liquid therethrough. As shown in FIG. 26, the valving surface 194 passes through the axis of rotation 200 of the valve member 150.

The dimensions and location of the cavity 149 and valve element 150 are selected with respect to the passageway 153 so that the axis of rotation of the valve member 150 will be substantially tangential to one side of the passageway 153 with the interior surface of the cavity 149 being substantially tangential to a diametrically opposed point on the opposite side of the channel 153.

When the valve element 150 is in position to fully close the passageway 153, the portion of the valving surface 194 which is not interposed in the passageway 153 extends radially of the valve element 150 at an included angle of about 60° with respect to the direction of liquid flow through the passageway 153. The portion 202 of the valving surface 194 which is interposed in the passageway 153 defines a circular surface having a radius substantially equal to the radius of the passageway 153.

Referring to FIG. 27, the rotation of the valve element 150 in the direction indicated by the arrow 198 in FIG. 26 will produce the change in volume of liquid flow through the heat exchanger 18 as indicated by the curve 204. Thus, with the position of the valve element 150 as shown in FIG. 26 corresponding to 0° of rotation, the passageway 153 will be fully closed and maximum liquid will flow through the heat exchanger 18 as indicated by the curve 204. Rotation of the valve element 150 in the direction indicated by the arrow 198 will tend to open the passageway 153 allowing a by-pass flow therethrough and reducing the volume of liquid flow through the heat exchanger 18. As shown by the curve 204, the initial rotation of the valve element 150 will produce a relatively gradual change in liquid flow through the heat exchanger. However, between about 30° and about 60° of rotation of the valve element 150 the volume of liquid flow through the heat exchanger 18 will change rapidly. Thereafter, continued rotation of the valve element 150 will produce a decreasing change in the volume of liquid flow through the heat exchanger 18.

For the reasons explained hereinabove, the result of such non-linear change in liquid flow through the heat exchanger with rotation of the valve element 150 will tend to result in a linear change in temperature of the liquid flowing in the heat exchange garment 10 with rotation of the valve element 150 as shown by the curve 206 in FIG. 28. In other words, at the intermediate flow rates through the heat exchanger 18 where a greater temperature differential between incoming and outgoing liquid may occur due to the greater time of contact with the temperature source resulting from such intermediate flow rate more rapid changes in flow rate will occur. At very low flow rates, such temperature differential may be larger, but the total volume of liquid will be less and thus changes in flow rate need not be accelerated. Thus, according to the preferred embodiment of applicant's invention, the user of applicant's system will be able to obtain a change in temperature in the heat exchange garment 10 that is substantially linearly related to a change in setting of the control knob 151.

Referring to FIGS. 29 through 34, the structural details of a heat exchanger 18 according to a preferred embodiment of this invention are shown. As best shown in FIGS. 29 and 32, the exterior of the heat exchanger 18 is defined by a luggage type case 210 and lid 212, made of rigid abrasion resistant material and each defining generally rectangular open sided hollow box elements hinged to each other along one of their open side edges 213. Latch means 214 and 215 are provided at the opposite open side edges of the case 210 and lid 212 elements, respectively, to enable the case to be quickly and easily opened as shown in FIG. 32 and closed as shown in FIG. 29. As best shown in FIGS. 30, 31 and 33, the interior of the case 210 and lid 212 each contain a body 216 and 217 respectively, of thermal insulating material. As best shown in FIGS. 32 and 33, each of the bodies 216 and 217 has a centrally disposed generally rectangular depression formed therein which cooperate to define a cavity 218 dimensioned to loosely receive a temperature source 56 in the form of a sealed generally rectangular can of frozen liquid, for example.

As best shown in FIGS. 31 and 33, a sealed liner 222 is interposed between the temperature source 56 and the interior surface of the cavity 218. The liner 222 provides for the conduction of liquid about the temperature source 56 in heat exchange relation thereto.

Referring to FIG. 34, the liner 222 according to the preferred embodiment of this invention comprises two overlying rectangular panels of 10 mil thick urethane film. The panels are dimensioned to extend over the sides and bottoms of the depressions in the bodies 216 and 217 which form the cavity 218. The panels are heat sealed to each other along their sides and also along their ends and have sufficient length to provide mounting tabs 224 at their ends. The panels are also heat sealed to each other along a narrow central portion 226 of their length extending from the first sealed end thereof to a point spaced from the second sealed end thereof to provide a generally U-shaped liquid passageway between the two panels.

An inlet elbow coupling 228 is sealed through an opening in one of the panels adjacent the first sealed end thereof and into communication with one leg of the U-shaped liquid passageway. Similarly, an outlet elbow coupling 229 is sealed through an opening in such panel at the first end thereof and into communication with the other leg of the U-shaped passageway.

As best shown in FIGS. 30 and 31, a quick disconnect coupling 232 mounted on the case 210 communicates with the inlet elbow 228 through an appropriate conduit 234. Similarly, a second quick disconnect coupling 233 mounted on the case 210 communicates with the outlet elbow 229 through an appropriate conduit 235. Thus, liquid from the third quick disconnect coupling 48 of the control display unit 20 may be conducted to the quick disconnect coupling 232 and circulated through the bladder 222, exiting from the quick disconnect coupling 233 for conduction back to the fourth quick disconnect coupling 52 of the control display unit 20. Such liquid will be under pressure provided by the pump 26 thereby forcing the bladder 222 into intimate contact with the can 220 of frozen liquid to provide for heat exchange therewith. It has been found to be unnecessary to provide more than one channel for liquid flow in the bladder 222 thus enabling the use of a simple bladder as described hereinabove.

As best shown in FIGS. 30 and 31, male snap type coupling elements 236 project from the bottom or back of the case 210 to enable the heat exchanger 18 to be removably mounted on the support panel 120 of the support harness 16. Thus the male elements 236 cooperate with the second array of fasteners 122 on the support panel 120 to enable heat exchanger 18 to be carried on the support harness 16 as shown in FIG. 1C. A similar arrangement may be used to enable the heat exchanger 18 to be carried on a belt as shown in FIG. 1D.

Where the heat exchanger 18 is to be hand-carried for mounting on a fixed support bracket 23 as shown in FIG. 1E, or where a fixed control display unit 20' is mounted on an immobile heat exchanger 58 as shown in FIG. 1F, it is desirable to provide an automatic quick disconnect coupling 24 as shown in FIGS. 1E and 1F. An automatic quick disconnect coupling according to the preferred embodiment of this invention is shown in FIGS. 35–36.

Referring to FIG. 35, an automatic quick disconnect coupling 24 according to the teaching of this invention may be easily assembled using simple and inexpensive accessory parts manufactured to fit the quick disconnect couplings used in the system. According to the preferred embodiment of this invention, for example, all of the quick disconnect couplings may be of the type manufactured and sold by Hoffman Engineering Company under the designation S2-M for the female portion 240 of the coupling and SP2-MV for the male portion 241 of the coupling. As is well known in the prior art, both the male and female portions of such couplings include a spring-loaded valve member adapted to seal the couplings against the flow of liquid therethrough when they are not in engagement with each other. As is also well known in the prior art, the female coupling 240 includes a spring-loaded collar 242 which must be retracted in order to allow the insertion or removal of the male portion 241 of the coupling.

According to the teaching of this invention, the automatic quick disconnect coupling includes a pair of mounting plates 244 and 245, an actuation member 246 and an acutation cable 247.

As shown in FIG. 37, one 245 of the pair of mounting plates has a pair of holes therethrough each for receiving the shank of a different one of a pair of male coupling members 241. As is well known in the prior art, the shank of each male coupling member 241 is then sealingly inserted into a different one of a pair of conduits 249. The shank of each male coupling member 241 is adapted to firmly grip the interior of the conduit 249 associated therewith and thus the mounting plate 245 is gripped firmly between the end of the conduits 249 and the coupling members 241.

The other mounting plate 244 may be a mirror image of the mounting plate 245 having a pair of holes therethrough, each adapted to receive the shank of a different one of a pair female coupling members 240 therethrough for insertion into a pair of associated conduits 248 as described hereinabove in connection with the male coupling elements 241. However, the mounting plate 244 is also provided with a hole therethrough centrally disposed between the two female coupling members 240 for receiving the actuation cable 247 therethrough.

The actuation member 246 is a plate-like member having a pair of apertures therethrough, each adapted to receive the collar 242 of a different one of the female coupling members 240 with a force fit whereby the collars 242 of both female coupling members 240 and the actuation member 246 are rigidly interconnected to move as a unit. The actuation member 246 is also provided with a hole therethrough disposed centrally between the collars 242 for receiving the actuation cable 247 therethrough. An appropriate stop member 250 is affixed to the actuation cable 247 to prevent it from being drawn through the hole in the actuation member 246 in the direction of the mounting plate 244.

Referring to FIGS. 37 and 38, the mounting plate 245 is provided with a hole 252 therethrough and the actuation member 246 is provided with guide pin 256 dimensioned to be received in the hole 252. The hole 252 and guide pin 256 are in alignment with each other and offset to one side of the pairs of coupling members 240 and 241. The guide pin 256 has a length sufficient to cause it to project through the hole 252 in the mounting plate 245 when the male coupling members 241 are in coupling engagement with the female coupling members 240. Thus, the guide pin 256 will make it impossible to bring the coupling members 240 and 241 into engagement in more than one orientation of the pairs thereof with respect to each other.

Referring to FIG. 36, the actuation cable 247 according to the teaching of this invention has a length not substantially greater, and preferably somewhat shorter than the length of the conduits 248. The end of the actuation cable 247 remote from the actuation member 246 is rigidly fixed by an appropriate means adjacent the ends of the conduits 248 remote from the mounting plate 244. Thus with the coupling 24 in its engaged position as shown in FIG. 36, inlet and outlet fluid flow will be reliably established therethrough. However, if the couduits 249 are subjected to tension forces, such forces will be conducted to the actuation cable 247 which will tend to cause the actuation member 246 and the collars 242 of the female coupling members 240 to move toward the mounting plate 244, thereby releasing the male coupling members 241 from their coupling engagement. It will be understood that the actuation cable 247 must be strong enough to resist any substantial elongation thereof under tension. The conduits 248 and 249 may be made of a material which will elongate under tension provided they have sufficient ultimate strength to withstand the tension necessary to produce the required movement of the actuation plate 246 and collars 242 to release the coupling 24.

The conduits 249 would normally comprise the inlet and outlet conduits to the heat exchange garment 10. Thus, movement of the user of the garment 10 away from the coupling 24 can produce sufficient tension in the conduits 249 to result in the automatic actuation of the quick disconnect couplings in an emergency requiring the user of the personal temperature control system of applicant's invention to disconnect himself from the system in order to escape a life threatening situation.

It is believed that persons skilled in the art will make obvious modifications in the preferred embodiments of this invention as shown in the drawing and described hereinabove without departing from the scope of the following claims. Specifically, various combinations of the elements of applicant's system may be made as claimed.

What is claimed is:

1. A temperature control system for the human body, adapted to be carried on the body of the user comprising:

a first heat exchanger in the form of a garment including a helmet and a separate body vest adapted to be worn by a user and connected together by a fluid conduit, each of the helmet and the body vest including a body of heat conducting material with an elongated fluid-tight passageway, adapted to conduct heat away from the head and torso of the user when worn thereon in heat-conducting relationship;

a second heat exchanger having means for receiving a source of cooling and including a body of heat conducting material with an elongated fluid-tight passageway, positioned to be in heat-conducting relationship with the source of cooling and being portable and having means for supporting it on the human body;

a first coolant conduit loop within which the first heat exchanger garment is positioned, including outlet conduit means from the heat exchanger garment and inlet conduit means to the heat exchanger garment and a bypass conduit extending between the outlet and inlet conduit means, the helmet being positioned upstream of the vest in the first heat exchange garment, whereby the coolant entering the garment from the inlet conduit means is first directed to the helmet and circulates through a series of channels throughout the helmet and is thereby warmed somewhat by heat exchange in the helmet before passing through the vest, so that the temperature differential between the coolant and the human body is less in the vest than in the helmet;

a pump in the first conduit loop, in one of said outlet conduit means and said inlet conduit means and between the heat exchanger garment and the bypass conduit, positioned to pump coolant liquid through the first heat exchanger garment from the inlet conduit means to the outlet conduit means;

a coolant liquid reservoir having an inlet and an outlet positioned in the first coolant conduit loop and containing coolant liquid;

a second coolant conduit loop within which the second heat exchanger is positioned, including said bypass conduit as part of the second conduit loop;

quick-disconnect means for joining the second heat exchanger into the second conduit loop whereby the second heat exchanger may be easily removed from the loop and replaced by another heat exchanger;

adjustable flow valve means connected in the bypass conduit, for adjusting the proportion of liquid coolant flowing from the outlet conduit means through (a) the second coolant conduit loop and (b) the bypass conduit, such valve being adjustable so that all, none or any proportion of the liquid coolant may be directed through the bypass conduit with the remainder, if any, being directed through the second coolant conduit loop, whereby the setting of the adjustable flow valve means regulates the extent to which coolant liquid warmed in the first heat exchanger garment is cooled in the second heat exchanger for return to the heat exchanger garment, and portability means for securing the liquid reservoir, the pump, the bypass conduit and the adjustable flow valve means on the body of the user whereby the system is easily carried by the user for movement through hostile, high-temperature environments.

2. The temperature control system of claim 1, wherein the vest includes series of heat exchange channels running generally horizontally and connected so that coolant entering the vest is directed first to the upper portions of the vest and travels progressively downwardly through the heat exchange channels and ultimately through the lower portions of the vest, so that the temperature differential between the coolant and the human body is less in the lower portions of the vest than in the upper portions of the vest, avoiding vaso-constriction and increasing comfort to the user.

3. The temperature control system of claim 1, further including a flow restrictor in the outlet conduit means, positioned to maintain a higher pressure in the coolant in the first heat exchanger garment than in the second heat exchanger.

4. The temperature control system of claim 1, wherein the system is sealed and the coolant liquid reservoir comprises a hollow liquid-tight container made of flexible material with a wall thickness selected to provide expansion/contraction flexure of the container when it is subjected to a differential of internal and external pressures of about two pounds per square inch, whereby venting to atmosphere is avoided.

5. The temperature control system of claim 1, wherein the coolant liquid reservoir, the pump, the bypass conduit and the adjustable flow valve means are contained in a common and portable control housing separate from the garment and the second heat exchanger, the housing providing conduit portions and quick-disconnect coupling means for connecting the pump ultimately to the heat exchanger garment and for connecting the outlet conduit means ultimately to an upstram end of the bypass conduit.

6. The temperature control system of claim 1, wherein the second heat exchanger comprises a pair of bodies made of thermal insulating material each having a centrally disposed depression formed therein, said pair of bodies and said depression being adapted to cooperate to define a cavity dimensioned to loosely receive a selected temperature source, and a linear interposed between the interior surface of said cavity and said selected temperature source received therein, said linear comprising two overlying panels of plastic film dimensioned to extend over the interior surface of said cavity, the panels being sealed to each other about their sides and ends and along a narrow central portion extending from one of the sealed ends to a point spaced from the other of the sealed ends thereof to provide said elongated fluid-tight passageway of said second heat exchange, whereby the second heat exchanger is light in weight and efficient in operation, enabling the portability of the temperature control system.

7. A method for cooling the human body, with a portable cooling system adapted to be carried on the human body, comprising:

providing a first heat exchanger garment to be worn by a person, including a heat exchanger helmet worn on the head and a separate heat exchanger vest worn on the torso, the two being interconnected in series relationship, the helmet being positioned upstream of the vest in the first heat exchange garment, whereby the coolant entering the garment is first directed to the helmet and circulates through a series of channels throughout the helmet and circulates through a series of channels throughout the helmet and is thereby warmed somewhat by heat exchange in the helmet before passing through the vest, so that the temperature differential between the coolant and the human body is less in the vest than in the helmet;

providing a compact portable housing unit attachable to the person and carried by the person, including a coolant liquid reservoir and a pump connected to the reservoir, providing a second heat exchanger in a portable form, with means for supporting it on the human body, carried by the person and including means for receiving a source of cooling and for exchanging heat between the source and a fluid-tight passageway within the second heat exchanger, interconnecting the first heat exchanger garment, the portable housing and the second heat exchanger by conduits with quick-disconnect couplings, so as to establish a first coolant conduit loop within which the first heat exchanger garment is positioned, and the first conduit loop including an inlet conduit to the heat exchanger garment and an outlet conduit from the heat exchanger garment and the reservoir and the pump within the first conduit loop, and also including a bypass conduit extending between the inlet and outlet conduits with the pump between the heat exchanger garment and the bypass conduit, and with an adjustable flow valve connected in the bypass conduit and contained in the portable housing unit to control the flow of coolant liquid through the bypass conduit, and so as to establish a second coolant conduit loop within which the second heat exchanger is positioned, including the bypass conduit as part of the second heat exchanger loop, the bypass valve being adjustable so that all, none or any proportion of the liquid coolant may be directed through the bypass conduit with the remainder, if any, being directed through the second coolant conduit loop, providing coolant liquid in the reservoir, the heat exchangers and the conduits, providing a source of cooling in the second heat exchanger, circulating coolant liquid with the pump, through the reservoir and the first coolant conduit loop and through the second coolant conduit loop, adjusting the adjustable flow valve to proportion the amount of coolant which (a) exits the first conduit loop and flows through the second conduit loop to be cooled in the second heat exchanger, and (b) flows through the bypass conduit and returns through the first conduit loop, to thereby regulate the amount of cooling of the coolant in the second heat exchanger and to set the coolant temperature in the helmet and vest at a selectable comfortable level for the person.

8. The method of claim 7, wherein the source of cooling is ice.

9. The method of claim 7, wherein the system is sealed and the coolant liquid reservoir comprises a hollow liquid-tight container made of flexible material with a wall thickness selected to provide expansion/contraction flexure of the container when it is subjected to a differential of internal and external pressures of about two pounds per square inch, whereby venting to atmosphere is avoided.

10. The method of claim 7, wherein only the head and torso of the person are cooled and wherein the adjustable flow valve is regulated manually to bring and maintain the head and torso temperatures to near normal, causing the person's extremities to also be at near normal temperatures.

11. A temperature control system for the human body, adapted to be carried on the body of the user, comprising:

a first heat exchanger in the form of a garment including a body vest adapted to be worn by a user, the body vest including a body of heat conducting mayterial with an elongated fluid-tight passageway, adapted to conduct heat away from the head and torso of the user when worn thereon in heat-conducting relationship;

a second heat exchanger having means for receiving a source of cooling and including a body of heat conducting material with an elongated fluid-tight passageway, positioned to be in heat-conducting relationship with the source of cooling and being portable and having means for supporting it on the human body;

a first coolant conduit loop within which the first heat exchanger garment is positioned, including outlet conduit means from the heat exchanger garment and inlet conduit means to the heat exchanger garment and a bypass conduit extending between the outlet and inlet conduit means;

the vest including series of heat exchange channels running generally horizontally and connected so that coolant entering the vest is directed first to the upper portions of the vest and travels progressively downwardly through the heat exchange channels and ultimately through the lower portions of the vest, so that the temperature differential between the coolant and the human body is less in the lower portions of the vest than in the upper portions of the vest, avoiding vaso-constriction and increasing comfort to the user;

a pump in the first conduit loop, in said inlet conduit means and between the heat exchanger garment and the bypass conduit, positioned to pump coolant liquid through the first heat exchanger garment from the inlet conduit means to the outlet conduit means;

a coolant liquid reservoir having an inlet and an outlet positioned in the first coolant conduit loop and containing coolant liquid, the system being sealed and the coolant liquid reservoir comprising a hollow liquid-tight container made of flexible material with a wall thickness selected to provide expansion/contraction flexure of the container when it is subjected to a differential of internal and external pressures, whereby venting to atmosphere is avoided;

a second coolant conduit loop within which the second heat exchanger is positioned, including said bypass conduit as part of the second conduit loop;

the second heat exchanger comprising a liner of two panels of plastic film sealed to each other along their sides and ends to provide a fluid tight passageway through which the coolant flows, the liner enveloping and contacting a cooling source whereby heat exchange occurs between the coolant and the cooling source;

a flow restrictor in the outlet conduit means, positioned to maintain a higher pressure in the coolant in the first heat exchanger garment than in the second heat exchanger;

adjustable flow valve means connected in the bypass conduit, for adjusting the proportion of liquid coolant flowing from the outlet conduit means through (a) the second coolant conduit loop and (b) the bypass conduit, such valve being adjustable so that all, none or any proportion of the liquid coolant may be directed through the bypass conduit with the remainder, if any, being directed through the second coolant conduit loop;

a portable housing wherein the coolant liquid reservoir, the pump, the bypass conduit and the adjustable flow valve means are contained separate from the garment and the second heat exchanger, the housing providing conduit portions and quick-disconnect coupling means for connecting the pump ultimately to the heat exchanger garment and for connecting the outlet means ultimately to an upstream end of the bypass conduit; and means for securing the portable housing on the body of the user, whereby the system is easily carried by the user for movement through hostile, high-temperature environments.

12. A temperature control system for the human body, adapted to be carried on the body of the user, comprising:

a first heat exchanger in the form of a garment including a helmet adapted to be worn by a user, the helmet including a body of heat conducting material with an elongated fluid-tight passageway, adapted to conduct heat away from the head of the user when worn thereon in heat-conducting relationship;

a second heat exchanger having means for receiving a source of cooling and including a body of heat conducting material with an elongated fluid-tight passageway, positioned to be in heat-conducting relationship with source of cooling;

a first coolant conduit loop within which the first heat exchanger garment is positioned, including outlet conduit means from the heat exchanger garment and inlet conduit means to the heat exchanger garment and a bypass conduit extending between the outlet and inlet conduit means;

a pump in the first conduit loop, in said inlet conduit means and between the heat exchanger garment and the bypass conduit, positioned to pump coolant liquid through the first heat exchanger garment from the inlet conduit means to the outlet conduit means;

a coolant liquid reservoir having an inlet and an outlet positioned in the first coolant conduit loop and containing coolant liquid;

the system being sealed and the coolant liquid reservoir comprising a hollow liquid-tight container made of flexible material with a wall thickness selected to provide expansion/contraction flexure of the container when it is subjected to a differential of internal and external pressures, whereby venting to atmosphere is avoided;

a second coolant conduit loop within which the second heat exchanger is positioned, including said bypass conduit as part of the second conduit loop;

the second heat exchanger comprising a liner of two panels of plastic film sealed to each other along their sides and ends to provide a fluid tight passageway through which the coolant flows, the liner enveloping and contacting a cooling source whereby a heat exchange occurs between the coolant and the cooling source;

a flow restrictor in the outlet conduit means, positioned to maintain a higher pressure in the coolant in the first heat exchanger garment than in the second heat exchanger;

adjustable flow valve mans connected in the bypass conduit, for adjusting the proportion of liquid coolant flowing from the outlet conduit means through (a) the second coolant conduit loop and (b) the bypass conduit, such valve being adjustable so that all, none or any proportion of the liquid coolant may be directed through the bypass conduit with the remainder, if any, being directed through the second coolant conduit loop;

a portable housing mans wherein the coolant liquid reservoir, the pump, the bypass conduit and the adjustable flow valve means are contained separated from the garment and the second heat exchanger, the housing providing conduit portions and quick-disconnect coupling means for connecting the pump ultimately to the heat exchanger garment and for connecting the outlet means ultimately to an upstream end of the bypass conduit; and means for carrying the portable housing means and the second heat exchanger on the body of the user, whereby the system is easily carried by the user for movement through hostile, high-temperature environments.

* * * * *